(12) United States Patent
Thomson et al.

(10) Patent No.: US 12,410,404 B2
(45) Date of Patent: Sep. 9, 2025

(54) HUMAN PLURIPOTENT STEM CELL-BASED SCREENING FOR SMOOTH MUSCLE CELL DIFFERENTIATION AND DISEASE

(71) Applicant: WISCONSIN ALUMNI RESEARCH FOUNDATION, Madison, WI (US)

(72) Inventors: James A. Thomson, Madison, WI (US); Jue Zhang, Madison, WI (US)

(73) Assignee: Wisconsin Alumni Research Foundation (WARF), Madison, WI (US)

(*) Notice: Subject to any disclaimer, the term of this patent is extended or adjusted under 35 U.S.C. 154(b) by 523 days.

(21) Appl. No.: 16/940,090

(22) Filed: Jul. 27, 2020

(65) Prior Publication Data
US 2020/0354681 A1 Nov. 12, 2020

Related U.S. Application Data

(62) Division of application No. 16/029,068, filed on Jul. 6, 2018, now Pat. No. 10,760,057.

(60) Provisional application No. 62/529,307, filed on Jul. 6, 2017.

(51) Int. Cl.
| | |
|---|---|
| C12N 5/077 | (2010.01) |
| A61K 31/4375 | (2006.01) |
| C12N 5/0735 | (2010.01) |

(52) U.S. Cl.
CPC ........ *C12N 5/0661* (2013.01); *A61K 31/4375* (2013.01); *C12N 5/0606* (2013.01); *C12N 2501/115* (2013.01); *C12N 2501/135* (2013.01); *C12N 2501/15* (2013.01); *C12N 2501/155* (2013.01); *C12N 2501/16* (2013.01); *C12N 2501/165* (2013.01); *C12N 2501/42* (2013.01); *C12N 2501/999* (2013.01); *C12N 2506/02* (2013.01); *C12N 2506/03* (2013.01); *C12N 2506/04* (2013.01); *C12N 2510/00* (2013.01); *C12N 2533/90* (2013.01)

(58) Field of Classification Search
None
See application file for complete search history.

(56) References Cited

U.S. PATENT DOCUMENTS

| | | |
|---|---|---|
| 8,268,620 B2 | 9/2012 | Thomson |
| 8,440,461 B2 | 5/2013 | Thomson |
| 2004/0063745 A1 | 4/2004 | Gellibert |
| 2004/0063949 A1 | 4/2004 | Gellibert |
| 2013/0217117 A1 | 8/2013 | Thomson |
| 2014/0057355 A1 | 2/2014 | Thomson |

FOREIGN PATENT DOCUMENTS

| | | |
|---|---|---|
| WO | 1998045479 | 10/1998 |
| WO | WO 2012/172328 A1 * | 12/2012 |

OTHER PUBLICATIONS

Keller et al., Jul. 28, 2016 (US 20160215263 A1).*
Bajpai, V.K., et al. (2012). Functional vascular smooth muscle cells derived from human induced pluripotent stem cells via mesenchymal stem cell intermediates. Cardiovasc Res 96, 391-400.
Beamish, J.A., et al. (2010). Molecular regulation of contractile smooth muscle cell phenotype: implications for vascular tissue engineering. Tissue Eng Part B Rev 16, 467-491.
Brown, M.E., et al. (2018). A Humanized Mouse Model Generated Using Surplus Neonatal Tissue. Stem Cell Reports 10, 1175-1183.
Brozovich, F.V., et al. (2016). Mechanisms of Vascular Smooth Muscle Contraction and the Basis for Pharmacologic Treatment of Smooth Muscle Disorders. Pharmacol Rev 68, 476-532.
Cao, N., et al. (2013). Highly efficient induction and long-term maintenance of multipotent cardiovascular progenitors from human pluripotent stem cells under defined conditions. Cell Res 23, 1119-1132.
Chen, G., et al. (2017). Unimolecular Micelle-Based Hybrid System for Perivascular Drug Delivery Produces Long-Term Efficacy for Neointima Attenuation in Rats. Biomacromolecules 18, 2205-2213.
Cheung, C., et al. (2012). Generation of human vascular smooth muscle subtypes provides insight into embryological origin-dependent disease susceptibility. Nat Biotechnol 30, 165-173.
Cong, L., et al. (2013). Multiplex genome engineering using CRISPR/Cas systems. Science 339, 819-823.
Couffinhal, T., et al., Mouse Model of aniogenesis, Am J Pathol 152, 1667-1679 (1998).
Dangas, G., et al. (2002). Cardiology patient page. Restenosis: repeat narrowing of a coronary artery: prevention and treatment. Circulation 105, 2586-2587.
Dash, B.C., et al. (2015). Induced pluripotent stem cellderived vascular smooth muscle cells: methods and application. Biochem J 465, 185-194.
De Vries, M.R., et al. (2016). Vein graft failure: from pathophysiology to clinical outcomes. Nat Rev Cardiol 13, 451-470.
DeRose, J.J., Jr., et al. (1999). Retinoic acid suppresses intimal hyperplasia and prevents vessel remodeling following arterial injury. Cardiovasc Surg 7, 633-639.
Ebert, A.D., et al. "Induced pluripotent stem cells from a spinal muscular atrophy patient." Nature 457.7227 (2009): 277.
Fouillade, C., et al. (2012). Notch signalling in smooth muscle cells during development and disease. Cardiovasc Res 95, 138-146.
Gellibert F, et al. Identification of 1,5-naphthyridine derivatives as a novel series of potent and selective TGF-beta type I receptor inhibitors. J Med Chem. Aug. 26, 2004;47(18):4494-506.

(Continued)

*Primary Examiner* — Allison M Fox
(74) *Attorney, Agent, or Firm* — McDonnell Boehnen Hulbert and Berghoff LLP

(57) ABSTRACT

Methods of using a small molecule MYH11 agonist to inhibit intimal hyperplasia and to maintain a contractile phenotype in vitro and in vivo are described. Also described herein are methods for generating human contractile smooth muscle cells from human pluripotent stem cells under defined conditions in the presence of the small molecule MYH11 agonist.

17 Claims, 19 Drawing Sheets

(19 of 19 Drawing Sheet(s) Filed in Color)

(56) References Cited

OTHER PUBLICATIONS

Gulkarov, I., et al. (2009). Topical mitogen-activated protein kinases inhibition reduces intimal hyperplasia in arterialized vein grafts. J Surg Res 154, 150-156.

Hou, Z., et al. (2013). Efficient genome engineering in human pluripotent stem cells using Cas9 from Neisseria meningitidis. Proc Natl Acad Sci U S A 110, 15644-15649.

Howden, S.E., et al. "Genetic correction and analysis of induced pluripotent stem cells from a patient with gyrate atrophy." Proceedings of the National Academy of Sciences 108.16 (2011): 6537-6542.

Hughes, J.P., et al. (2011). Principles of early drug discovery. Br J Pharmacol 162, 1239-1249.

Ichida, J.K., et al. (2009). A small-molecule inhibitor of tgf-Beta signaling replaces sox2 in reprogramming by inducing nanog. Cell Stem Cell 5, 491-503.

James, D., et al. (2010). Expansion and maintenance of human embryonic stem cell-derived endothelial cells by TGFbeta inhibition is Id1 dependent. Nat Biotechnol 28, 161-166.

Karamariti, E., et al. (2013). Smooth muscle cells differentiated from reprogrammed embryonic lung fibroblasts through DKK3 signaling are potent for tissue engineering of vascular grafts. Circ Res 112, 1433-1443.

Kim et al., "Human peripheral blood-derived CD31+ cells have robust angiogenic and vasculogenic properties and are effective for treating ischemic vascular disease." Journal of the American College of Cardiology 56.7 (2010): 593-607.

Mack, C.P. (2011). Signaling mechanisms that regulate smooth muscle cell differentiation. Arterioscler Thromb Vasc Biol 31, 1495-1505.

Mali, P., et al. (2013). RNA-guided human genome engineering via Cas9. Science 339, 823-826.

Muto, A., et al. (2007). Smooth muscle cell signal transduction: implications of vascular biology for vascular surgeons. J Vasc Surg 45 Suppl A, A15-24.

Nabel, E.G., et al. (1993). Direct transfer of transforming growth factor beta 1 gene into arteries stimulates fibrocellular hyperplasia. Proc Natl Acad Sci U S A 90, 10759-10763.

Newby, A.C., et al. (2000). Molecular mechanisms in intimal hyperplasia. J Pathol 190, 300-309.

Owens, G.K., et al. (2004). Molecular regulation of vascular smooth muscle cell differentiation in development and disease. Physiol Rev 84, 767-801.

Pannu, H., et al. (2007). MYH11 mutations result in a distinct vascular pathology driven by insulin-like growth factor 1 and angiotensin II. Hum Mol Genet 16, 2453-2462.

Patsch, C., et al. (2015). Generation of vascular endothelial and smooth muscle cells from human pluripotent stem cells. Nat Cell Biol 17, 994-1003.

Pendyala, L., et al. (2008). Drug-eluting stents: present and future. Cardiovasc Hematol Agents Med Chem 6, 105-115.

Prasad, C.K., et al. (2005). Survival of endothelial cells in vitro on Paclitaxel-loaded coronary stents. J Biomater Appl 19, 271-286.

Raines, E.W. (2004). PDGF and cardiovascular disease. Cytokine Growth Factor Rev 15, 237-254.

Rensen, S.S., et al. (2007). Regulation and characteristics of vascular smooth muscle cell phenotypic diversity. Neth Heart J 15, 100-108.

Sawada, N., et al. (2000). Inhibition of rho-associated kinase results in suppression of neointimal formation of balloon-injured arteries. Circulation 101, 2030-2033.

Shi, X., et al. (2014). Periadventitial application of rapamycin-loaded nanoparticles produces sustained inhibition of vascular restenosis. PLoS One 9, e89227.

Suwanabol, P.A., et al. (2011). TGF-beta and restenosis revisited: a Smad link. J Surg Res 167, 287-297.

Thomson, et al., "Embryonic stem cell lines derived from human blastocysts." science 282.5391 (1998): 1145-1147.

Wanjare, M., et al. (2013). Derivation and maturation of synthetic and contractile vascular smooth muscle cells from human pluripotent stem cells. Cardiovasc Res 97, 321-330.

Wasteson, P., et al. (2008). Developmental origin of smooth muscle cells in the descending aorta in mice. Development 135, 1823-1832.

Wolf, Y.G., et al. (1994). Antibodies against transforming growth factor-beta 1 suppress intimal hyperplasia in a rat model. J Clin Invest 93, 1172-1178.

Yang, L., et al. (2016). Differentiation of Human Induced-Pluripotent Stem Cells into Smooth-Muscle Cells: Two Novel Protocols. PLoS One 11, e0147155.

Yu et al., "Induced pluripotent stem cell lines derived from human somatic cells." Science 318.5858 (2007): 1917-1920.

Yu et al., "Human induced pluripotent stem cells free of vector and transgene sequences." Science 324.5928 (2009): 797-801.

Zhang, J., et al. (2017). Functional characterization of human pluripotent stem cell-derived arterial endothelial cells. Proc Natl Acad Sci U S A 114, E6072-E6078.

Zhang, J., et al. (2011). A human iPSC model of Hutchinson Gilford Progeria reveals vascular smooth muscle and mesenchymal stem cell defects. Cell Stem Cell 8, 31-45.

Zheng, N., et al. (2014). Low concentration of rapamycin inhibits hemangioma endothelial cell proliferation, migration, and vascular tumor formation in mice. Curr Ther Res Clin Exp 76, 99-103.

* cited by examiner

HUMAN PLURIPOTENT STEM CELL-BASED SCREENING FOR SMOOTH MUSCLE CELL DIFFERENTIATION AND DISEASE

CROSS-REFERENCE TO RELATED APPLICATIONS

This application is a divisional of U.S. application Ser. No. 16/029,068, filed Jul. 6, 2018, which claims priority to U.S. Provisional Application No. 62/529,307, filed Jul. 6, 2017, each of which is incorporated by reference herein in their entirety.

STATEMENT REGARDING FEDERALLY SPONSORED RESEARCH

This invention was made with government support under TR000506 awarded by the National Institutes of Health. The government has certain rights in the invention.

BACKGROUND

Balloon angioplasty, stents, and bypass surgery are commonly used to treat occlusive arterial disease, a leading worldwide cause of morbidity and mortality (de Vries et al., 2016). However, restenosis occurs in a significant number of the treated patients who develop intimal hyperplasia (Beamish et al., 2010; Dangas and Kuepper, 2002), in connection with which contractile smooth muscle cells (SMCs) decrease contractile protein expression and increase proliferation, migration, and extracellular matrix (ECM) production, which is characteristic of synthetic smooth muscle cells (contractile-to-synthetic phenotypic switching) (Beamish et al., 2010; Rensen et al., 2007). Small molecules that promote maintenance of the contractile phenotype or promote differentiation of contractile SMCs at the expense of synthetic SMCs (i.e., inhibit or reverse contractile-to-synthetic phenotypic switching) could minimize the development of intimal hyperplasia.

TGF-β1 and/or PDGF-BB are widely used to differentiate SMCs from human pluripotent stem cells (Bajpai et al., 2012; Cao et al., 2013; Cheung et al., 2012; Dash et al., 2015; Karamariti et al., 2013; Patsch et al., 2015; Wanjare et al., 2013; Yang et al., 2016; Zhang et al., 2011). However, up-regulation of PDGF-BB and TGF-β1 signaling promotes contractile-to-synthetic phenotypic SMC switching (Muto et al., 2007; Nabel et al., 1993; Newby and Zaltsman, 2000; Raines, 2004; Suwanabol et al., 2011; Wolf et al., 1994). As a result, if SMCs used in tissue engineered vascular constructs are generated from pluripotent stem cells using PDGF-BB and TGF-β1, the SMCs carry a risk of causing intimal hyperplasia.

SUMMARY OF THE INVENTION

In a first aspect, provided herein is a method of obtaining smooth muscle cells. In some embodiments, the smooth muscle cells are human smooth muscle cells or mammalian smooth muscle cells. The method comprises culturing SMC progenitor cells in a culture medium that comprises an MYH11 agonist, whereby a cell population comprising contractile smooth muscle cells is obtained. The cell population can comprise at least 80% contractile smooth muscle cells. The contractile smooth muscle cells can express one or more markers selected from the group consisting of MYH11, SMA, SM22α, ACTA2, SMTN, CNN1, and ELN. In some embodiments, the SMC progenitor cells are cultured for 12 days to obtain a cell population comprising contractile smooth muscle cells.

In some embodiments of the first aspect, the SMC progenitor cells are obtained by a method comprising (i) culturing mesoderm cells under conditions and for a time sufficient to obtain a population of cells expressing MEOX1; (ii) culturing the population of cells expressing MEOX1 under conditions and for a time sufficient to suppress MEOX1 expression; and (iii) culturing the population of cells from step (ii) under conditions and for a time sufficient to obtain a population of SMC progenitor cells.

In some embodiments, in step (i) the mesoderm cells are cultured in chemically defined medium comprising TGFβ1 in an amount sufficient to obtain a population of cells expressing MEOX1. In some embodiments, the mesoderm cells are cultured for 18 hours.

In some embodiments, in step (ii) the MEOX1-expressing cells are cultured in chemically defined medium comprising a fibroblast growth factor (FGF) or a vascular endothelial growth factor (VEGF) in an amount sufficient to suppress MEOX1 expression. In some embodiments, the MEOX1-expressing cells are cultured for 5 days. In some embodiments, the FGF is FGF2.

In some embodiments, in step (iii) the population of cells from step (ii) are cultured in chemically defined medium comprising FGF2 and VEGFA for a period of time sufficient to induce SMC progenitor cells. In some embodiments, in step (iii) the chemically defined medium additionally comprises a NOTCH agonist. In some embodiments, the NOTCH agonist is RESV. In some embodiments, the cells from step (ii) are cultured for at least about 2 days. In some embodiments, the cells from step (ii) are cultured for at least about 4 days.

In some embodiments, the SMC progenitor cells are obtained by a method comprising: (i) culturing mesoderm cells in chemically defined medium that comprises a fibroblast growth factor (FGF) or a vascular endothelial growth factor (VEGF) for about 5 days; and (ii) culturing the population of cells from step (i) under conditions and for a time sufficient to obtain a population of SMC progenitor cells. In some embodiments, the FGF is FGF 2. In some embodiments, the population of cells from step (i) are cultured in chemically defined medium comprising FGF2 and VEGFA for a period of time sufficient to induce SMC progenitor cells. In some embodiments, the cells of step (i) are cultured for at least about 2 days. In some embodiments the population of cells from step (i) are cultured in chemically defined medium that additionally comprises RESV.

In some embodiments of the first aspect, the mesoderm cells are obtained by culturing human pluripotent stem cells for a period of about two days in a chemically defined cell culture medium comprising a Bone Morphogenetic Protein (BMP), Activin A, and an activator of Wnt/β-catenin signaling to obtain a cell population comprising mesodermal cells. In some embodiments, the pluripotent stem cells are human embryonic stem cells. In some embodiments, the pluripotent stem cells are human induced pluripotent stem cells.

In some embodiments of the first aspect, the MYH11 agonist is selected from the group consisting of imatinib, sorafenib, OSI-930, DCC-2036, SB590885, indirubin, RG108, tranylcypromine hydrochloride, GSK182497A, GSK282449A, GSK607049C, GSK1023156A, RepSox, ABS 205, flurbiprofen, sitagliptin, BI-1356, hydroflumethiazide, sulfacetamide sodic hydrate, minoxidil, sulfaphenazole, fusaric acid, nisoldipine, NAT16-352622, NAT15-330204, NAT13-338612, NAT6-298378, NAT18-

381960, NAT18-355551, NAT6-324295, NAT23-390920, NAT31-470153, NAT37-510679, T0520-3169, T5341423, T5342130, T5343121, T5216652, and forskolin. In some embodiments, the MYH11 agonist is RepSox. In one embodiment, the culture medium comprises 25 μM RepSox.

In a second aspect, provided herein is a substantially pure, isolated population of contractile smooth muscle cells obtained according to the methods described herein. The isolated population of contractile smooth muscle cells can comprise at least 90% contractile smooth muscle cells.

In a third aspect, provided herein is a tissue engineered blood vessel comprising the isolated cell population of contractile smooth muscle cells obtained according to the methods described herein.

In a fourth aspect, provided herein is a tissue engineered construct comprising the isolated cell population of contractile smooth muscle cells obtained according to the methods described herein.

In a fifth aspect, provided herein is a method of treatment comprising administering to a subject in need thereof a therapeutically effective amount of the isolated cell population of MYH11 positive contractile smooth muscle cells. In some embodiments, the MYH11 positive contractile smooth muscle cells are obtained according to the methods described herein. In some embodiments, the method of treatment is a method of treating intimal hyperplasia.

In a sixth aspect, provided herein is a method of treatment of intimal hyperplasia comprising administering to a subject in need thereof a therapeutically effective amount of an MYH11 agonist. In some embodiments, the MYH11 agonist is RepSox.

BRIEF DESCRIPTION OF DRAWINGS

The patent or patent application file contains at least one drawing in color. Copies of this patent or patent application publication with color drawings will be provided by the Office upon request and payment of the necessary fee.

FIG. 1A shows a schematic of high-throughput screening of 4804 small molecules to determine their suitability for generating contractile smooth muscle cells and for anti-restenosis drug discovery. The MYH11-Nluc-2A-Tom reporter human ES cell line was differentiated into mesoderm by culture for two days in E8BAC medium (E8 medium supplemented with 5 ng/ml BMP4, 25 ng/ml Activin A, and 1 μM CHIR99021) then treated with 50 ng/ml FGF2 and 20 ng/ml BMP4 in E6 medium (E8 medium minus FGF2 and TGFβ1). The cells were passaged at day 4 and seeded on the 96-well plate for screening ($2 \times 10^6$ cells/plate). After the reporter cell line was differentiated into mesoderm, small molecules were added to the cells from day 4 to day 14. FIG. 1B depicts the results of the screening in two batches. The luciferase assay results of individual small molecules were normalized to the average reads of all samples for each batch. The small molecules were selected for further analysis when the normalized reads were greater than "average+3×STDEV". FIG. 1C depicts optimizing the concentration of the selected small molecules.

FIG. 2A shows a schematic of the optimized SMC differentiation protocol. The MYH11-NLuc-2A-Tom reporter human ES cell line was differentiated into mesoderm by using E8BAC medium (E8 medium supplemented with 5 ng/ml BMP4, 25 ng/ml Activin A and 1 CHIR99021) for 36 hours and then treated for 18 hours with 1.7 ng/ml TGF-β1 in E6 medium to induce expression of MEOX1. For the next 5 days, MEOX1 expression was suppressed in the cells by culture in FGF2 (100 ng/ml) in E5 medium (See Table 1). Next, the cells were treated from day 8-12 with FGF2 (100 ng/ml), VEGFA (50 ng/ml) and RESV (5 μM, a NOTCH agonist) in E6 medium to induce SMC progenitors. Then, to further mature the SMC progenitors into SMCs, the progenitor cells were cultured from day 12 until day 24 in RESV (in E6 medium) supplemented with various combinations of RepSox (25 μM), PDGF-BB (10 ng/ml), and TGF-β1 (1.7 ng/ml). FIG. 2B shows flow cytometric analysis of MYH11-Tom+ cells. RepSox-SMCs represents SMCs induced by RepSox; P-SMCs represents SMCs induced by PDGF-BB; T-SMCs represents SMCs induced by TGF-β1; and PT-SMCs represent SMCs induced by TGF-β1 and PDGF-BB. FIG. 2C shows MYH11-Tom+ cell statistics. Data are represented as mean±standard deviation (SD). Data as analyzed using Student's t-test, *: P<0.05, n=3. FIG. 2D shows live imaging of MYH11-Tom expression. Scale bar=1 mm. FIG. 2E shows immunostaining of SMA and SM22α. Scale bar=50 μm. FIG. 2F shows RT-qPCR of SMCs. Data are represented as mean±SD. Student's t-test, *: P<0.05, n=3.

FIG. 3A shows Click-iT EdU analysis of cell proliferation. FIG. 3B shows statistics data of EdU incorporated cells represented as mean±SD. Student's t-test, n=4, *: P<0.05, compared to P-SMCs and primary human aortic SMCs (AoSMCs). FIG. 3C shows cell migration. Cells were imaged at 0 and 24 hours. FIG. 3D shows statistics data of cell migration represented as mean±SD. Student's t-test, n=4, *: P<0.05, vs all the other SMCs. Scale bar=400 μm. FIG. 3E depicts the cell contraction assay. Cells were imaged before and after the treatment with 100 μM carbachol. Arrows indicate the contracting cells. Scale bar=100 μm. Statistics data of cell surface changes are represented as mean±SD. Student's t-test, *: P<0.05, vs all the other SMCs. n=65, 61, 56, 59, and 53 cells for RepSox-SMCs, P-SMCs, T-SMCs, PT-SMCs, and AoSMCs, respectively. FIG. 3G demonstrates a kidney capsule experiment. SMCs were transplanted in the kidney of severe combined immunodeficiency (SCID) mice. Images represents triple immunostaining of anti-SMA (labeling smooth muscle cells), anti-hu-nuclear (labeling human cells), and anti-Ki67 (labeling proliferating cells). Scale bar=100 FIG. 3H shows triple immunostaining of anti-SMA (labeling smooth muscle cells), anti-hu-nuclear (labeling human cells), and anti-CD31 (labeling endothelial cells). Scale bar=100 μm. FIGS. 3I-3K show statistics data for percentage of Ki67+ cells, SMA+ cells, and CD31 coverage of human cells in kidney capsule. Data were represented as mean±SD. Student's t-test, *: P<0.05.

FIG. 4A shows Click-iT EdU analysis of cell proliferation. FIG. 4B shows statistics data of EdU incorporated cells represented as mean±SD. Student's t-test, n=4 biological replicates. *: P<0.05. AoSMCs were treated with DMSO or 100 μM RepSox for two days. FIG. 4C shows cell migration. AoSMCs were treated with DMSO or 100 μM RepSox for two days before the migration assay and one additional day during the assay. Cells were imaged at 0 and 24 hours. FIG. 4D shows statistics data of migration cells represented as mean±SD. Student's t-test, n=6 samples from 3 biological replicates. *: P<0.05. Scale bar=500 μm. FIG. 4E shows the cell contraction assay. AoSMCs were treated with DMSO or 100 μM RepSox for two days before adding 100 μM carbachol. Cells were imaged before and after the carbachol treatment. Scale bar=100 μm. FIG. 4F shows statistics data of cell surface changes represented as mean±SD. Student's t-test, *: P<0.05, n=50 cells/group. Arrows indicate the contraction cells. FIG. 4G shows RT-qPCR of SMCs. AoSMCs were treated with DMSO or 100 μM RepSox for three days. Data are represented as mean±SD. Student's t-test, *: P<0.05, n=3 biological replicates.

FIG. 5A depicts the rat balloon injury experiment. H&E staining is shown. Arrowheads indicate the intima. Scale bar=200 μm. FIG. 5B shows statistics data of intima/media ratio represented as mean±SD. Student's t-test, n=5 animals/group, from 2 independent experiments. *: P<0.05. FIG. 5C shows RT-qPCR of endothelial cell marker expression. Student's t-test, n=3*: P<0.05. FIG. 5D shows double immunostaining of anti-SMA and anti-PCNA (labeling endothelial cells). Scale bar=100 Neointima is highlighted. Red arrows indicate the region with high SMA expression. Yellow arrows indicate the region with low SMA expression. FIG. 5E shows statistics data of proliferation represented as mean±SD. Student's t-test, n=3*: P<0.05, ns: non-significant. FIG. 5F shows immunostaining of MYH11 expression. Red arrows indicate the region with high MYH11 expression. Yellow arrows indicate the region with low MYH11 expression. FIG. 5G shows immunostaining of SM22α. Red arrows indicate the region with high SM22α expression. Yellow arrows indicate the region with low SM22α expression. FIG. 5H shows statistics data of SMA, MYH11, or SM22α expression. The "% of high expression"=ratio of "area of high expression"/"total area of intima and media". Data are represented as mean±SD. Student's t-test, n=3*: P<0.05. FIG. 5I shows TUNEL assay (labeling apoptotic cells). Scale bar=100 Neointima is highlighted. FIG. 5J shows statistics data of apoptosis represented as mean±SD. Student's t-test, n=3*: P<0.05, ns: non-significant.

FIG. 6A shows a schematic of wild type and targeted MYH11-NLuc-2A-tdTomato allele. P1-4 indicate the locations of PCR primers used and B represents the BamH1 cut site. FIG. 6B shows junction PCR of the 5' arm and 3' arm of MYH11-NLuc-2A-tdTomato allele. WT: wild type, KI: Knock-in cells. FIG. 6C shows a southern blot of MYH11-NLuc-2A-tdTomato allele. FIG. 6D shows qPCR analysis of tdTomato (Tom) copy number. Data are represented as mean±SD. n=3. Con: control samples with one copy of Tom. FIG. 6E shows qPCR analysis of MYH11 expression in cells sorted by flow cytometry. Data are represented as mean±SD. n=3. FIG. 6F shows karyotyping of MYH11-NLuc-2A-Tom cell line. FIG. 6G shows immunostaining showing the overlapped expression of endogenous MYH11 and Knock-in tdTomato. Scale bar=100 μm. FIG. 6H shows live imaging showing the overlapped expression of tdTomato and NanoLuc Luciferase. Scale bar=50 μm.

FIG. 7A shows flow cytometric analysis of MYH11-Tom+ cells after treated with RepSox (25 μM) or SB431542 (10 μM) from day 10-14. Data are represented as mean±SD, n=3 biological replicates. *, p<0.05, student t-test. FIG. 7B shows qPCR analysis of CNN1 and MYH11 expression. Cells were treated with RepSox (25 μM) or SiRNA. Comb3: Knockdown of TGFBR1, ACVR1B, and ACVR1C at the same time. Data are represented as mean±SD, n=2 biological replicates. *, p<0.05, student t-test. FIG. 7C shows qPCR analysis of gene expression. Cells were treated with RepSox (25 μM) or SiRNA. Data are represented as mean±SD, n=2 biological replicates. *, p<0.05, student t-test. FIG. 7D shows a Western blot of NICD1, NOTCH1, pSMAD2, and GAPDH. During the smooth muscle cells differentiation, cells were treated with or without RepSox from day 10-11. FIG. 7E shows a Western blot of NICD1, NOTCH1, and GAPDH. During the smooth muscle cells differentiation, cells were treated with RepSox for 1 or 20 hours at day 12. FIG. 7F shows flow cytometric analysis of MYH11-Tom+ cells after treatment with DMSO, RepSox (25 DAPT (20 DBZ (10 μM), or RO4929097 (10 μM) from day 10-16. Data are represented as mean±SD, n=3 biological replicates. *, p<0.05, student t-test. FIG. 7G shows qPCR analysis of NOTCH1 and MYH11 expression. Cells were treated with RepSox and non-targeting control (NT)/SiRNA at day 10. The RNA was isolated at day 14.

FIG. 8A shows regulation of MEOX1 expression (RT-qPCR analysis), which labels the paraxial mesoderm that contributes smooth muscle cells (Wasteson et al., 2008). Cells were cultured in E8BAC medium (E8 medium supplemented with 5 ng/mL BMP4, 25 ng/mL Activin A, and 1 μM CHIR99021) for 36 hours and then cultured in E6 (E8 medium minus FGF2 and TGF-β1), E6T (E6+1.7 ng/ml TGF-β1), E6F (E6+100 ng/ml FGF2), or E6V (E6+50 ng/ml VEGFA) medium for another two days. Undifferentiated cells cultured in E8 medium were used as the control. Data are represented as mean±SD, n=3. *, p<0.05, student t-test. FIG. 8B shows that passaging cells promotes MEOX1 expression. Cells were cultured in E8BAC medium for 36 or 43 hours and then passaged or non-passaged as indicated. The cells were cultured in E6T beginning at 36 or 43 hours. Undifferentiated cells (0 h) were used as the control. Data are represented as mean±SD, n=3. *, p<0.05, student t-test. FIG. 8C shows optimization of the medium used from day 3-8. Cells were cultured in E8BAC medium for 36 hours and then passaged and cultured in E6T medium for another 18 hours. E5 (E8 medium minus FGF2, TGF-β1, and insulin) was used as the base medium from day 3-8. FGF (F), VEGFA (V), resveratrol (R), or insulin was added as indicated. Statistics of MYH11-Tom+ cells measured by flow cytometry at day 16. Data are represented as mean±SD. Student's t-test, *: P<0.05, n=3. FIG. 8D shows optimization of the medium used from day 8-12. E6 (E8 medium minus FGF2 and TGF-β1) was used as the base medium. FGF (F), VEGFA (V), or resveratrol (R) was added as indicated. Statistics of MYH11-Tom+ cells measured by flow cytometry at day 16. Data are represented as mean±SD. Student's t-test, *: P<0.05, n=3. FIG. 8E shows optimization of the medium used from day 12-16. Cells were treated with or without RepSox. Statistics of MYH11-Tom+ cells measured by flow cytometry at day 16. Data are represented as mean±SD. Student's t-test, *: P<0.05, n=3. FIG. 8F shows statistics of MYH11-Tom+ cells showing timing and differentiation efficiency. Data are represented as mean±SD. Student's t-test, *: P<0.05, n=3.

FIG. 9A shows flow cytometric analysis of MYH11-Tom+ cells derived from RepSox protocol or Cheung's protocol for LM-SMCs (Cheung et al., 2012). FIG. 9B shows qPCR analysis of MYH11 expression. Data are normalized to Cheung's LM-SMCs and represented as mean±SD, n=3 for all the samples except fresh human artery (n=2). *, p<0.05, student t-test.

FIG. 10A shows immunostaining of MYH11, SMA, and SM22α. Scale bar=50 μm. FIG. 10B show statistics of MYH11$^+$, SMA$^+$, and SM22α$^+$ cells measured by immunostaining. Data are represented as mean±SD. n=3. FIG. 10C shows RT-qPCR of SMCs. Data are normalized to H1-derived SMCs and represented as mean±SD. n=3.

FIG. 11A shows that RepSox-SMCs ($1\times10^7$ cells/animal) (labeled by tdTomato) were recruited by mouse endothelial cells (labeled by mCD31) in a mouse limb in a surgically-induced mouse hind limb ischemia model. Arrows indicate the recruited SMCs. Scale bar=50 µm. Right panel, a stacked bar graph showing the physiological status at post-operative day 35. n=10 animals for PBS group and 11 animals for SMCs group. *, P<0.05 (Chi-squared test). FIG. 11B shows the percentage of blood flow in a mouse hind limb ischemic model compared to the control leg for mice treated with SMCs or PBS.

INCORPORATION BY REFERENCE

All publications, including but not limited to patents and patent applications, cited in this specification are herein incorporated by reference as though set forth in their entirety in the present application.

DETAILED DESCRIPTION OF THE INVENTION

One strategy to overcome the problem of intimal hyperplasia, caused by either occlusive arterial disease treatments or PDGF and TGF-β signaling, is to use high-throughput screening to identify small molecules that can promote contractile SMC differentiation. Since normal vascular differentiation and the dedifferentiation observed in vascular disease share common pathways, this screening strategy using human pluripotent stem cell-SMC cell differentiation could identify drug candidates that prevent restenosis caused by intimal hyperplasia.

The present disclosure is based at least in part on the inventors' recognition that MYH11 agonists cause cells to maintain a contractile phenotype in vitro and in vivo. As described herein, MYH11 agonists inhibit intimal hyperplasia in vivo and when administered to cells in vitro, can promote synthetic-to-contractile phenotypic switching. In a first aspect, the present invention is a method for pluripotent cell differentiation into SMCs using an MYH11 agonist. In another aspect, the present invention is a method of treating or preventing intimal hyperplasia in a subject in need thereof using a therapeutic agent. It is contemplated that a therapeutic agent of the present invention may be selected from the group consisting of an MYH11 agonist, contractile smooth muscle cells obtained by the methods disclosed herein, tissue engineered blood vessels comprising the contractile smooth muscle cells obtained by the methods disclosed herein, and a larger tissue-engineered vascular construct comprising the contractile smooth muscle cells obtained by the methods disclosed herein.

Figures 1A, 1B, 1C:
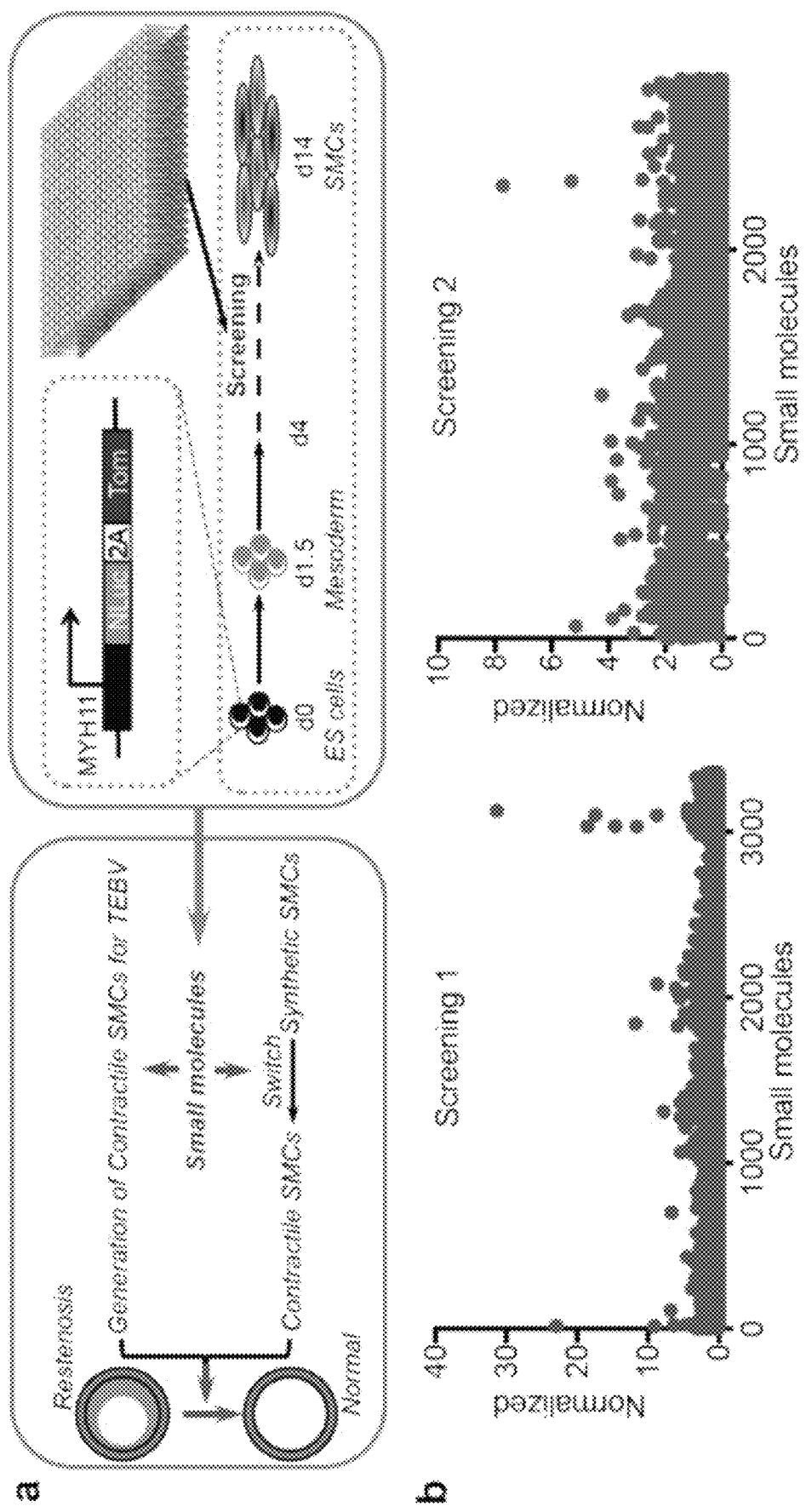
FIGS. 1A-1C depict a schematic of high-throughput screening.
Figures 1A, 1B, 1C:
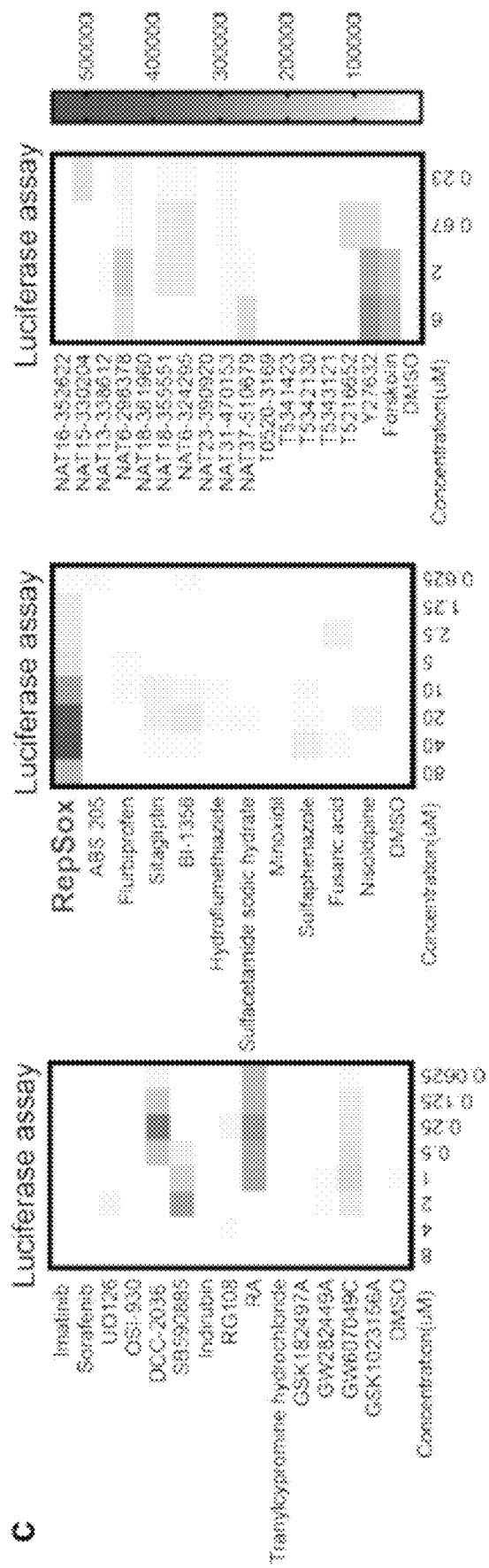

As used herein, the term "MYH11 agonist" refers to a small molecule listed in FIG. 1C that has been identified in the screen method described in FIG. 1A and Example 1 as a molecule that promotes MYH11$^+$ SMC differentiation. The MYH11 agonist is selected from the group consisting of imatinib, sorafenib, UO126, OSI-930, DCC-2036, SB590885, indirubin, RG108, retinoic acid, tranylcypromine hydrochloride, GSK182497A, GSK282449A, GSK607049C, GSK1023156A, RepSox, ABS 205, flurbiprofen, sitagliptin, BI-1356, hydroflumethiazide, sulfacetamide sodic hydrate, minoxidil, sulfaphenazole, fusaric acid, nisoldipine, NAT16-352622, NAT15-330204, NAT13-338612, NAT6-298378, NAT18-381960, NAT18-355551, NAT6-324295, NAT23-390920, NAT31-470153, NAT37-510679, T0520-3169, T5341423, T5342130, T5343121, T5216652, Y27632, and forskolin. In a preferred embodiment, the MYH11 agonist is RepSox. In some embodiments, the MYH11 agonist is also a NOTCH agonist.

As used herein, the term "RepSox" refers to the MYH11 agonist, NOTCH agonist, and TGFβR-1/ALK5 inhibitor shown at Formula I, and suitable derivatives thereof. Suitable derivatives of RepSox are active as a MYH11 agonist and are able to promote MYH11$^+$ SMC differentiation. RepSox derivatives are described in US Patent Publication No. 2004/0063949 and US Patent Publication No. 2004/0063745. RepSox is available commercially from R&D Systems.

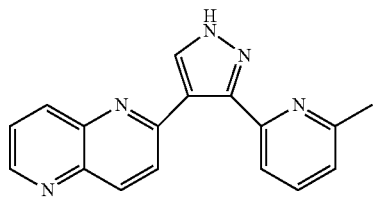

Formula I

The methods provided herein comprise differentiating human pluripotent stem cells under conditions that promote differentiation of the pluripotent stem cells into contractile smooth muscle cells. As used herein, the term "promote differentiation" is used to indicate conditions and medium which support differentiation to give rise to the indicated cell population of interest. As used herein, the term "smooth muscle cell" (SMC) refers to cells expressing MYH11, SMA, SM22α, ACTA2, SMTN, CNN1, and ELN. Contractile SMCs obtained by the methods of the present invention are characterized by high levels of expression of one or more of the contractile smooth muscle markers MYH11, SMA, SM22α, ACTA2, SMTN, CNN1, and ELN. Contractile SMCs are also characterized by a decrease in collagen expression. Contractile SMCs are distinguishable from synthetic SMCs on the basis of an increase in the expression of contractile genes and the production of less extracellular matrix (ECM), as well as lower proliferation and migration rate. In some embodiments, the SMCs are human SMCs.

In a first aspect, a method of producing a contractile smooth muscle cell comprises culturing human pluripotent stem cells in culture medium that promotes mesoderm differentiation. In one embodiment, a chemically defined culture medium that promotes mesoderm differentiation comprises Activin A, Bone Morphogenic Protein 4 (BMP4), FGF2, and an activator of Wnt/β-catenin signaling. In some embodiments, the activator of Wnt/β-catenin signaling is a Gsk3 inhibitor. In some embodiments the Gsk3 inhibitor is selected from the group consisting of CHIR99021, CHIR98014, BIO-acetoxime, BIO, LiCl, SB216763, SB415286, AR A014418, I-Azakenpaullone, and Bis-7-indolylmaleimide. In some embodiments the Gsk3 inhibitor is CHIR99021 or CHIR98014 at a concentration between about 0.5 µM to about 10 µM in the medium. In a preferred embodiment, the Gsk3 inhibitor is CHIR99021 at a concentration between about 0.5 µM to about 5 µM.

In exemplary embodiments, pluripotent stem cells are cultured in a medium comprising or consisting essentially of DMEM/F12 culture medium, L-ascorbic acid-2-phosphate magnesium, sodium selenium, human FGF2, insulin, NaHCO₃, transferrin, TGFβ1, BMP4, Activin-A, and CHIR99021 ("E8BAC medium") for 36 hours. Preferably, the culture medium comprises or consists essentially of DMEM/F12 medium; L-ascorbic acid-2-phosphate magnesium (64 mg/l); sodium selenium (14 µg/l); human FGF2 (100 µg/l); insulin (20 mg/l); NaHCO₃ (543 mg/l); transferrin (10.7 mg/l); TGFβ1 (2 µg/l); BMP4 (5 µg/l); Activin A (25 µg/l); and CHIR99021 (1 µM). In some embodiments, the medium is a chemically defined culture medium. In addition to DMEM/F12 medium, it is possible to use other base medium known in the art, for example, RPMI 1640. Additionally, inclusion of transferrin is optional. While CHIR99021 is not required, it is included to promote mesoderm formation. Human pluripotent stem cells are cultured in the culture medium for about 36 hours. After about 36 hours, at least about 80% (e.g., at least about 80%, 85%, 90%, 95%, 99%) of the resulting cell population are mesoderm cells. As used herein, the term "mesoderm cell" refers to a cell having mesoderm-specific gene expression, capable of differentiating into a mesodermal lineage such as bone, muscle such as cardiac muscle, skeletal muscle and smooth muscle (e.g., of the gut), connective tissue such as the dermis and cartilage, kidneys, the urogenital system, blood or hematopoietic cells, heart and vasculature. Mesoderm-specific biomarkers include Brachyury (7). Culturing can take place on any appropriate surface (e.g., in two-dimensional or three-dimensional culture).

Methods of the present invention further comprise directing differentiation of mesoderm cells into SMC progenitors. As used herein, the term "SMC progenitor" refers to cells that can give rise to SMCs but not other cell types. Culturing can take place on any appropriate surface (e.g., in two-dimensional or three-dimensional culture).

In exemplary embodiments, mesoderm cells are passaged and cultured at low cell density. Low cell density is considered to be a cell density such that 100% cell density will be achieved at about day 6 (e.g., day 5, 6, or 7). In some embodiments, mesoderm cells are cultured at a concentration of about $1.0 \times 10^4$ to $4.0 \times 10^4$ cell/cm² (e.g., about $1.0 \times 10^4$, $1.5 \times 10^4$, $2.0 \times 10^4$, $2.5 \times 10^4$, $3.0 \times 10^4$, $3.5 \times 10^4$, $4.0 \times 10^4$ cell/cm²) at passaging.

In exemplary embodiments, a method of obtaining SMC progenitors comprises a first step of culturing mesoderm cells in chemically defined medium comprising or consisting essentially of TGFβ1 in E6 medium for a length of time sufficient to induce expression of MEOX1. In exemplary embodiments, mesoderm cells are cultured in chemically defined medium comprising or consisting essentially of about 1.7 ng/ml TGFβ1 (e.g., about 1.0, 1.2, 1.5, 1.7, 1.9, 2.0 ng/ml), DMEM/F12 culture medium, L-ascorbic acid-2-phosphate magnesium, sodium selenium, insulin, NaHCO₃, and transferrin for about 18 hours (e.g., about 12, 15, 16, 17, 18, 19, 20, or 22 hours). The cell population produced from the first step will express MEOX1. As used herein, the term "MEOX1-expressing cell," refers to a cell expressing MEOX1. In some embodiments, the MEOX1-expressing cell population is selected from the group consisting of paraxial mesoderm cells and somatic mesoderm cells. Culturing can take place on any appropriate surface (e.g., in two-dimensional or three-dimensional culture). In some embodiments, cells are cultured on a MATRIGEL™ substrate (BD Biosciences, NJ) according to the manufacturer's protocol, on a vitronectin substrate, or on a Corning® Synthemax surface.

In exemplary embodiments, a method of obtaining SMC progenitors comprises culturing MEOX1 expressing cells obtained, e.g., as above, in chemically defined medium that comprises or consists essentially of FGF2 in E5 medium for about 5 days (e.g., about 3, 4, 5, 6, 7, 8, 9, or 10 days) to suppress MEOX1 expression. In exemplary embodiments, the MEOX1 expressing cells from the first step are cultured in chemically defined medium that comprises or consists essentially of about 100 ng/ml FGF2 (e.g., about 80, 90, 95, 100, 110 ng/ml), DMEM/F12 culture medium, L-ascorbic acid-2-phosphate magnesium, sodium selenium, NaHCO₃, and transferrin for about 5 days. In some embodiments, the FGF2 may be replaced with a different fibroblast growth factor (FGF) or a vascular endothelial growth factor (VEGF), for example FGF1 or VEGFB. In some embodiments, MEOX1 expression is suppressed by at least about 75%, at least about 80%, at least about 85%, at least about 90%, or at least about 95%, relative to the MEOX1 expressing cells before culturing in chemically defined medium comprising FGF2. Culturing can take place on any appropriate surface (e.g., in two-dimensional or three-dimensional culture). In some embodiments, cells are cultured on a MATRIGEL™ substrate (BD Biosciences, NJ) according to the manufacturer's protocol, on a vitronectin substrate, or on a Corning® Synthemax surface.

Alternatively, mesoderm cells may be cultured directly in chemically defined medium that comprises or consists essentially of FGF2 in E5 medium for about 5 days (e.g., about 3, 4, 5, 6, 7, 8, 9, or 10 days) without the first step of culturing in E6 medium with TGFβ1. In exemplary embodiments, the mesoderm cells are cultured in chemically defined medium that comprises or consists essentially of about 100 ng/ml FGF2 (e.g., about 80, 90, 95, 100, 110 ng/ml), DMEM/F12 culture medium, L-ascorbic acid-2-phosphate magnesium, sodium selenium, NaHCO₃, and transferrin for about 5 days. In some embodiments, the FGF2 may be replaced with a different fibroblast growth factor (FGF) or a vascular endothelial growth factor (VEGF), for example FGF1 or VEGFB. Culturing can take place on any appropriate surface (e.g., in two-dimensional or three-dimensional culture). In some embodiments, cells are cultured on a MATRIGEL™ substrate (BD Biosciences, NJ) according to the manufacturer's protocol, on a vitronectin substrate, or on a Corning® Synthemax surface. The population of cells produced by culturing mesoderm cells for about 5 days in chemically defined culture medium comprising FGF2 can then be cultured in the present of FGF2 and VEGFA as described below to produce a population of cells comprising SMC progenitors.

In exemplary embodiments, a method of obtaining SMC progenitors comprises a third step of culturing the cells from the second step in chemically defined medium comprising or consisting essentially of FGF2 and VEGFA in E6 medium for a length of time sufficient to induce SMC progenitors. In some embodiments, the chemically defined medium used in the third step may optionally include a NOTCH agonist. The NOTCH agonist can be selected from the group consisting of Resveratrol (3,4',5-trihydroxystilbene, RESV), valproic acid, and suberoyl bishydroxamic acid. In exemplary embodiments, the cell population produced from the second step is cultured in chemically defined medium comprising or consisting essentially of FGF2 (100 ng/ml), VEGFA (50 ng/ml), DMEM/F12 culture medium, L-ascorbic acid-2-phosphate magnesium, sodium selenium, insulin, NaHCO₃, and transferrin for at least about 2 days (e.g., about 2, 3, 4, 5, or 6 days). In some embodiments, the cell population produced from the second step is cultured in chemically defined medium comprising or consisting essentially of FGF2 (100 ng/ml), VEGFA (50 ng/ml), DMEM/F12 culture medium, L-ascorbic acid-2-phosphate magnesium, sodium selenium, insulin, NaHCO$_3$, and transferrin for at least about 4 days. In some embodiments, the chemically defined medium optionally includes RESV (5 µM). Culturing can take place on any appropriate surface (e.g., in two-dimensional or three-dimensional culture). In some embodiments, cells are cultured on a MATRIGEL™ substrate (BD Biosciences, NJ) according to the manufacturer's protocol, on a vitronectin substrate, or on a Corning® Synthemax surface.

Methods of the present invention further comprise directing differentiation of SMC progenitors to SMCs. In exemplary embodiments, a method of obtaining SMCs comprises culturing SMC progenitors in an SMC differentiation medium comprising or consisting essentially of an MYH11 agonist in E6R medium (See Table 1) where culturing occurs for a length of time sufficient for the cultured SMC progenitors to differentiate into SMCs. In exemplary embodiments, SMC progenitors are cultured in chemically defined medium comprising or consisting essentially of an MYH11 agonist, RESV (5 DMEM/F12 culture medium, L-ascorbic acid-2-phosphate magnesium, sodium selenium, insulin, NaHCO$_3$, and transferrin for at least about 12 days (e.g., about 8, 9, 10, 11, 12, 13, 14, or 15 days). In some embodiments, the MYH agonist is RepSox and the SMC progenitors are cultured in chemically defined medium comprising or consisting essentially of about 25 µM RepSox (e.g., about 15, 20, 25, 30 or 35 RESV (5 DMEM/F12 culture medium, L-ascorbic acid-2-phosphate magnesium, sodium selenium, insulin, NaHCO$_3$, and transferrin for about 12 days (e.g., about 8, 9, 10, 11, 12, 13, 14, or 15 days). As demonstrated in the examples included herein RepSox acts as a NOTCH agonist in the present methods, and other NOTCH agonists may also have the same activity in the present methods. Culturing can take place on any appropriate surface (e.g., in two-dimensional or three-dimensional culture). In some embodiments, cells are cultured on a MATRIGEL™ substrate (BD Biosciences, NJ) according to the manufacturer's protocol, on a vitronectin substrate, or on a Corning® Synthemax surface.

For several of the biological markers described herein, expression will be low or intermediate in level. While it is commonplace to refer to cells as "positive" or "negative" for a particular marker, actual expression levels are a quantitative trait. The number of molecules on the cell surface can vary by several logs, yet still be characterized as "positive." Accordingly, characterization of the level of staining permits subtle distinctions between cell populations. Expression levels can be detected or monitored by flow cytometry, where lasers detect the quantitative levels of fluorochrome (which is proportional to the amount of cell surface antigen bound by the antibodies). Flow cytometry or fluorescence-activated cell sorting (FACS) can be used to separate cell populations based on the intensity of antibody staining, as well as other parameters such as cell size and light scatter. Although the absolute level of staining may differ with a particular fluorochrome and antibody preparation, the data can be normalized to a control.

Any appropriate method can be used to detect expression of biological markers characteristic of cell types described herein. For example, the presence or absence of one or more biological markers can be detected using, for example, RNA sequencing (e.g., RNA-seq), immunohistochemistry, polymerase chain reaction, qRT-PCR, or other technique that detects or measures gene expression. RNA-seq is a high-throughput sequencing technology that provides a genome-wide assessment of the RNA content of an organism, tissue, or cell. Alternatively, or additionally, one may detect the presence or absence or measure the level of one or more biological markers of SMCs using, for example, fluorescent in situ hybridization; (FISH; see WO98/45479 published October, 1998), Southern blotting, Northern blotting, or polymerase chain reaction (PCR) techniques, such as real time quantitative PCR (RT-PCR). In exemplary embodiments, a cell population obtained according to a method provided herein is evaluated for expression (or the absence thereof) of biological markers of smooth muscle cells such as MYH11, SMA, SM22α, ACTA2, SMTN, CNN1, and ELN. Preferably, SMCs express one or more of the following smooth muscle cell markers: MYH11, SMA, SM22α, ACTA2, SMTN, CNN1, and ELN. Quantitative methods for evaluating expression of markers at the protein level in cell populations are also known in the art. For example, flow cytometry is used to determine the fraction of cells in a given cell population that express or do not express biological markers of interest.

The methods provided herein produce isolated populations of SMCs, where the isolated population is a substantially pure population of SMCs. As used herein, "isolating" and "isolated" refer to separating, selecting, or enriching for a cell type of interest or subpopulation of cells from surrounding, neighboring, or contaminating cells or from cells of another type. As used herein, the term "substantially pure" refers to a population of cells that is at least about 75% (e.g., at least about 75%, 85%, 90%, 95%, 98%, 99% or more) pure, with respect to SMCs making up a total cell population. In other words, the term "substantially pure" refers to a population of SMCs of the present invention that contains at least about 75%, 80%, 90%, or 95% of SMCs when directing differentiation to obtain cells of the contractile smooth muscle cell lineage. The term "substantially pure" also refers to a population of SMCs of the present invention that contains fewer than about 20%, about 10%, or about 5% of non-SMCs in an isolated population prior to any enrichment, expansion step, or differentiation step. In some cases, a substantially pure isolated population of SMCs generated according to a method provided herein is at least about 95% (e.g., at least about 95%, 96%, 97%, 98%, 99%) pure with respect to SMCs making up a total cell population.

In some embodiments, the proportion of contractile smooth muscle cells in a population of cells obtained in the described methods is enriched using a cell separation, cell sorting, or enrichment method, e.g., fluorescence activated cell sorting (FACS), enzyme-linked immunosorbent assay (ELISA), magnetic beads, magnetic activated cell sorting (MACS), laser-targeted ablation of non-endothelial cells, and combinations thereof. Preferably, FACS is used to identify and separate cells based on cell-surface antigen expression.

As used herein, "pluripotent stem cells" appropriate for use according to a method of the invention are cells having the capacity to differentiate into cells of all three germ layers. Suitable pluripotent cells for use herein include human embryonic stem cells (hESCs) and human induced pluripotent stem (iPS) cells. As used herein, "embryonic stem cells" or "ESCs" mean a pluripotent cell or population of pluripotent cells derived from an inner cell mass of a blastocyst. See Thomson et al., *Science* 282:1145-1147 (1998). These cells express Oct-4, SSEA-3, SSEA-4, TRA-1-60 and TRA-1-81. Pluripotent stem cells appear as compact colonies comprising cells having a high nucleus to cytoplasm ratio and prominent nucleolus. ESCs are commercially available from sources such as WiCell Research Institute (Madison, Wis.). As used herein, "induced pluripotent stem cells" or "iPS cells" mean a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs, as described herein. See, e.g., Yu et al., *Science* 318:1917-1920 (2007).

Induced pluripotent stem cells exhibit morphological properties (e.g., round shape, large nucleoli and scant cytoplasm) and growth properties (e.g., doubling time of about seventeen to eighteen hours) akin to ESCs. In addition, iPS cells express pluripotent cell-specific markers (e.g., Oct-4, SSEA-3, SSEA-4, Tra-1-60 or Tra-1-81, but not SSEA-1). Induced pluripotent stem cells, however, are not immediately derived from embryos. As used herein, "not immediately derived from embryos" means that the starting cell type for producing iPS cells is a non-pluripotent cell, such as a multipotent cell or terminally differentiated cell, such as somatic cells obtained from a post-natal individual.

Human iPS cells can be used according to a method described herein to obtain SMCs having the genetic complement of a particular human subject. For example, it may be advantageous to obtain SMCs that exhibit one or more specific phenotypes associated with or resulting from a particular disease or disorder of the particular mammalian subject. In such cases, iPS cells are obtained by reprogramming a somatic cell of a particular human subject according to methods known in the art. See, for example, U.S. Patent Publication No. 2013/0217117, U.S. Patent Publication No. 2014/0057355, U.S. Pat. Nos. 8,268,620, 8,440,461, Yu et al., *Science* 324(5928):797-801 (2009); Chen et al., *Nat. Methods* 8(5):424-9 (2011); Ebert et al., *Nature* 457(7227): 277-80 (2009); Howden et al., *Proc. Natl. Acad. Sci. U.S.A.* 108(16):6537-42 (2011). Induced pluripotent stem cell-derived SMCs allow modeling of drug responses in tissue constructs that recapitulate vascular tissues in an individual having, for example, a particular disease. Even the safest drugs may cause adverse reactions in certain individuals with a specific genetic background or environmental history. Accordingly, human subject specific iPS cell-derived SMCs are useful to identify genetic factors and epigenetic influences that contribute to variable drug responses.

Subject-specific somatic cells for reprogramming into iPS cells can be obtained or isolated from a target tissue of interest by biopsy or other tissue sampling methods. In some cases, subject-specific cells are manipulated in vitro prior to use in the methods of the present invention. For example, subject-specific cells can be expanded, differentiated, genetically modified, contacted to polypeptides, nucleic acids, or other factors, cryo-preserved, or otherwise modified prior to use in the methods described herein.

Media and substrate conditions for culturing pluripotent stem cells, as used in the methods described herein, are well known in the art. In some cases, pluripotent stem cells to be differentiated according to the methods disclosed herein are cultured in mTESR-1® medium (StemCell Technologies, Inc., Vancouver, British Columbia), or Essential 8® medium (Life Technologies, Inc.) on a MATRIGEL™ substrate (BD Biosciences, NJ) according to the manufacturer's protocol or on a Corning® Synthemax surface.

Preferably, human pluripotent stem cells (e.g., human ESCs or iPS cells) are cultured in the absence of a feeder layer (e.g., a fibroblast feeder layer), a conditioned medium, or a culture medium comprising poorly defined or undefined components. As used herein, the terms "chemically defined medium" and "chemically defined culture medium" also refer to a culture medium containing formulations of fully disclosed or identifiable ingredients, the precise quantities of which are known or identifiable and can be controlled individually. As such, a culture medium is not chemically defined if (1) the chemical and structural identity of all medium ingredients is not known, (2) the medium contains unknown quantities of any ingredients, or (3) both. Standardizing culture conditions by using a chemically defined culture medium minimizes the potential for lot-to-lot or batch-to-batch variations in materials to which the cells are exposed during cell culture. Accordingly, the effects of various differentiation factors are more predictable when added to cells and tissues cultured under chemically defined conditions.

As used herein, the term "serum-free" refers to cell culture medium or cell culture conditions that do not contain serum or serum replacement and that are free of serum obtained from animal (e.g., fetal bovine) blood or other biological materials. For avoidance of doubt, serum-containing medium is not chemically defined. Likewise, an "albumin free" culture medium means a medium that does not contain albumin or is essentially free of albumin.

In general, culturing cells or tissues in the absence of animal-derived materials (i.e., under xenogen-free conditions) reduces or eliminates the potential for cross-species viral or prion transmission. As used herein, the terms "xenogen-free" and "xeno-free" are used interchangeably and refer to cell or tissue culture conditions that avoid the use of xenogeneic materials including, without limitation, animal-derived cells, exudates, or other constituents of animal (e.g., non-human) origin. As used herein, the term "xeno-free" also refers to a medium free of any cell or cell product of a species other than that of the cultured cell. Human proteins are preferred but not essential for chemically defined conditions, provided that uncharacterized animal products are excluded.

The methods of the present invention provide scalable, inexpensive, and reproducible generation of human SMCs. For instance, after obtaining a cell population comprising human SMCs according to a method described herein, the human SMC population can be expanded in a culture medium appropriate for proliferating human SMCs. In some embodiments, the culture medium used for proliferating human SMCs is E6R medium supplemented with an MYH11 agonist. In one embodiment, the culture medium used for proliferating human SMCs is E6R medium supplemented with RepSox.

TABLE 1

Chemically Defined Culture Medium Components

| Medium Name | Protocol Step | Chemically Defined Components |
|---|---|---|
| E8 | | DMEM/F12 medium + L-ascorbic acid-2-phosphate magnesium (64 mg/l); sodium selenium (14 µg/l); FGF2(100 µg/l); insulin (20 mg/l); NaHCO$_3$ (543 mg/l); Transferrin (10.7 mg/l); and TGFβ1 (2 µg/l) |
| E8BAC | Human pluripotent stem cells to mesoderm cells | E8 medium + BMP4 (5 µg/l); Activin A (25 µg/l); and CHIR99021 (1 µM) |
| E7 | | DMEM/F12 medium + L-ascorbic acid-2-phosphate magnesium (64 mg/l); sodium selenium (14 µg/l); FGF2 (100 µg/l); insulin (20 mg/l); NaHCCE (543 mg/l); and Transferrin (10.7 mg/1) |
| E7BVi | | E7 medium + VEGFA (50 µg/l); BMP4 (50 µg/l); and SB431542 (5 µM) |
| E7Bi | | E7 medium + BMP4 (50 µg/l); and SB431542 (5 µM) |
| E7Vi | | E7 medium + VEGFA (50 µg/l); and SB431542 (5 µM) |
| E7V | | E6 medium + FGF2 100 µg/l; and 50 µg/l VEGFA |
| E6 | | DMEM/F12 medium + L-ascorbic acid-2-phosphate magnesium (64 mg/l); sodium selenium (14 µg/l); insulin (20 mg/l); NaHCO$_3$ (543 mg/l); and transferrin (10.7 mg/l) |
| E6T | Mesoderm cells to MEOX1 expressing cells | E6 + TGFβ1 (1.7 ng/ml) |
| E5F | MEOX1 suppression | E5 + FGF2 (100 µg/l) |
| E6FVB | | E6 medium + FGF2(100 µg/l); VEGFA (50 µg/l); and BMP4 (50 µg/l) |
| E6V | | E6 medium + VEGFA (50 µg/l) |
| E6FVR | Induction of SMC progenitors | E6 medium + FGF2 (100 µg/l) VEGFA (50 µg/l) RESV (5 µM) |
| E6R | | E6 + RESV (5 µM) |
| R + Rep | Maturation of contractile SMCs | E6R + RepSox (25 µM) |
| E5 | | DMEM/F12 medium + L-ascorbic acid-2-phosphate magnesium (64 mg/1); sodium selenium (14 µg/l); NaHCO$_3$ (543 mg/1); and transferrin (10.7 mg/1) |
| FVIRL | | E5 medium + FGF2 (100 µg/l) VEGF-165 (50 µg/l) SB431542(10 µM) RESV (5 µM) L-690,330 (10 µM) |
| FVIRLW | | FVIRL + WNT3A 100 (ng/ml) |
| FVIRL-5 | | E5 medium + FGF2 (100 µg/l); VEGF-165 (50 µg/l); SB431542(10 µM); RESV (5 µM); and L-690,330 (5 µM) |
| FVIRL-5-I | | FVIRL-5 + insulin (20 mg/1) |
| FVIRL-5-W | | FVIRL-5 + WNT3A (50 ng /ml) |
| FVIRL-5-BB | | FVIRL-5 + PDGF-BB (100 ng/ml) |
| FVIR | | E5 medium + FGF2 (100 µg/l); VEGF-165 (50 µg/l); SB431542(10 µM); and RESV (5 µM) |
| FVIL | | E5 medium + FGF2 (100 µg/l); VEGF-165 (50 µg/l); SB431542(10 µM); and L-690,330 (10 µM) |

TABLE 1-continued

Chemically Defined Culture Medium Components

| Medium Name | Protocol Step | Chemically Defined Components |
| --- | --- | --- |
| FVIW | | E5 medium + FGF2 (100 µg/l); VEGF-165 (50 µg/l); SB431542 (10 µM); and WNT3A (100 ng/ml) |
| FVB | | E5 medium + FGF2 (100 µg/l); VEGF-165 (50 µg/l); and BMP4 (50 µg/l) |
| FVI | | E5 medium + FGF2 (100 µg/l); VEGF-165 (50 µg/l); and SB431542 (10 µM) |
| FV | | E5 medium + FGF2 (100 µg/l) VEGF-165 (50 µg/l) |
| BVIn | | E5 medium + BMP4 (50 µg/l); VEGF-165 (50 µg/l) Insulin (20 mg/l) |
| VI | | E5 medium + VEGF-165 (50 µg/l) SB431542 (5 µM) |
| Control | | E5 medium FGF2 (100 µg/l) SB431542 (10 µM) |
| Control + VEGF | | Control medium + VEGF-165 (50 ng/ml) |
| Control + RESV | | Control medium + RESV (5 µM) |
| Control + WNT3A | | Control medium + WNT3A (50 ng/ml) |

In another aspect, provided herein is a method for producing an engineered blood vessel using smooth muscle cells obtained according to a method provided herein. SMCs also can be used as raw materials, possibly in combination with additional cell populations, for creating blood vessels in vitro or in vivo. Such vessels will be useful, for example, in revascularizing damaged tissues and in treating peripheral artery disease. Engraftment of and vasculogenesis by externally injected cells has been shown by in vivo animal studies. See, for example, Kim et al., *J. Am. Coll. Cardiol.* 56: 593-607 (2010). Additionally it is envisioned that SMCs can be used for vascular disease modeling, such as intimal hyperplasia.

Treatment

In another aspect, provided herein are therapeutic compositions including a therapeutic agent and methods of using them for the treatment of subjects. A therapeutic agent of the present invention is selected from the group consisting of an MYH11 agonist, RepSox, smooth muscle cells obtained according to the methods provided herein, tissue engineered blood vessels comprising SMCs obtained according to the methods provided herein, and tissue-engineered constructs comprising SMCs obtained according to the methods provided herein.

In a further aspect, therefore, the present invention provides methods and compositions for cell transplantation, cell replenishment, and cell or tissue replacement. The method can comprise providing to a subject in need thereof a therapeutically effective amount of contractile smooth muscle cells derived according to methods provided herein, whereby providing contractile smooth muscle cells treats the subject. In one aspect, an MYH11 agonist is administered to a subject in need thereof. In some embodiments, RepSox or a suitable variant thereof is administered to a subject in need of thereof. Subjects in need of treatment include those already having or diagnosed with intimal hyperplasia or those who are at risk of developing intimal hyperplasia.

Currently used anti-restenotic drugs, including rapamycin (and its analogs) and paclitaxel suppress endothelium repair. In contrast, RepSox has fewer side effects and is beneficial to endothelial cell recruitment and repair. Rep Sox also inhibits the proliferation of de-differentiated cells and prevents de-differentiation of cells in the intima. Furthermore, RepSox promotes intima apoptosis.

Disorders requiring cell or tissue replacement, improving vasculogenesis, and inhibiting intimal hyperplasia include, without limitation, restenosis, occlusive arterial disease, myocardial and peripheral vascular ischemia, other peripheral artery diseases, myocardial infarction (MI), stroke, and diabetic neuropathy, and any other disorder or disease for which the stricken individual would benefit from angiogenic regenerative medicine.

As used herein, the terms "treat" and "treating" refer to both therapeutic and prophylactic or preventive measures, wherein the object is to prevent or slow down (lessen) an undesired physiological change or pathological disorder resulting from intimal hyperplasia. For purposes of this invention, treating the intimal hyperplasia includes, without limitation, alleviating one or more clinical indications, reducing the severity of one or more clinical indications of intimal hyperplasia, diminishing the extent of the condition, stabilizing the intimal hyperplasia (i.e., not worsening), delaying or slowing, halting, or reversing the intimal hyperplasia, observing an increase in walking distance or walking speed, pain relief in a subject, and bringing about partial or complete remission of intimal hyperplasia. Treating the disease or injury also includes prolonging survival by days, weeks, months, or years as compared to prognosis if treated according to standard medical practice not incorporating treatment with the therapeutic agent.

Subjects in need of treatment can include those already having or diagnosed with intimal hyperplasia as well as those prone to, likely to develop, or suspected of having a disease or injury as described herein. Pre-treating or preventing a disease or injury according to a method of the present invention includes initiating the administration of a therapeutic agent (e.g., RepSox or SMCs obtained by the methods described herein) at a time prior to the appearance or existence of intimal hyperplasia, or prior to the exposure of a subject to factors known to induce intimal hyperplasia.

Pre-treating the disorder is particularly applicable to subjects at risk of having or acquiring intimal hyperplasia. As used herein, the terms "prevent" and "preventing" refer to prophylactic or preventive measures intended to inhibit undesirable physiological changes or the development of a disorder or condition resulting in the disease or injury. In exemplary embodiments, preventing the disease or injury comprises initiating the administration of a therapeutic agent (e.g., RepSox or SMCs obtained by the methods described herein) at a time prior to the appearance or existence of intimal hyperplasia such that intimal hyperplasia, or its symptoms, pathological features, consequences, or adverse effects do not occur. In such cases, a method of the invention for preventing intimal hyperplasia comprises administering RepSox or SMCs obtained by the methods described herein to a subject in need thereof prior to exposure of the subject to factors that influence the development of the intimal hyperplasia, such as, but not limited to, subjects receiving vascular grafts, bypass grafts, subjects undergoing balloon angioplasty procedures, subjects receiving stents, subjects undergoing bypass surgery, and the like.

As used herein, the terms "subject" or "patient" are used interchangeably and can encompass any vertebrate including, without limitation, humans, mammals, reptiles, amphibians, and fish. Preferred individual subjects according to the present invention are mammals including, without limitation, humans and non-human primates, as well as canines, felines, ovines, porcines, equines, and bovines. In exemplary embodiments, the subject is a human. As used herein, the phrase "in need thereof" indicates the state of the subject, wherein therapeutic or preventative measures are desirable. Such a state can include, but is not limited to, subjects having intimal hyperplasia, restenosis, occlusive arterial disease, or a pathological symptom or feature associated with intimal hyperplasia, restenosis, or occlusive arterial disease.

In some cases, a method of treating or preventing a disease or injury as described herein comprises administering a pharmaceutical composition comprising a therapeutically effective amount of a therapeutic agent (e.g., RepSox or SMCs obtained by the methods described herein). As used herein, the term "pharmaceutical composition" refers to a chemical or biological composition suitable for administration to a mammal. Examples of compositions appropriate for such therapeutic applications include preparations for parenteral, subcutaneous, transdermal, intradermal, intramuscular, intracoronarial, intramyocardial, intraperitoneal, intravenous (e.g., injectable), or intratracheal administration, such as sterile suspensions, emulsions, and aerosols. In some cases, pharmaceutical compositions appropriate for therapeutic applications may be in admixture with one or more pharmaceutically acceptable excipients, diluents, or carriers such as sterile water, physiological saline, glucose or the like. For example, the therapeutic agent can be administered to a subject as a pharmaceutical composition comprising a carrier solution.

Formulations may be designed or intended for oral, rectal, nasal, topical or transmucosal (including buccal, sublingual, ocular, vaginal and rectal) and parenteral (including subcutaneous, intramuscular, intravenous, intradermal, intraperitoneal, intrathecal, intraocular and epidural) administration. In general, aqueous and non-aqueous liquid or cream formulations are delivered by a parenteral, oral or topical route. In other embodiments, the compositions may be present as an aqueous or a non-aqueous liquid formulation or a solid formulation suitable for administration by any route, e.g., oral, topical, buccal, sublingual, parenteral, aerosol, a depot such as a subcutaneous depot or an intraperitoneal or intramuscular depot. In some cases, pharmaceutical compositions are lyophilized. In other cases, pharmaceutical compositions as provided herein contain auxiliary substances such as wetting or emulsifying agents, pH buffering agents, gelling or viscosity enhancing additives, preservatives, flavoring agents, colors, and the like, depending upon the route of administration and the preparation desired. The pharmaceutical compositions may be formulated according to conventional pharmaceutical practice (see, e.g., Remington: *The Science and Practice of Pharmacy,* 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, NY). The pharmaceutical composition for administration must be formulated, produced, and stored according to standard methods that provide proper sterility and stability.

The preferred route may vary with, for example, the subject's pathological condition or weight or the subject's response to therapy or that is appropriate to the circumstances. The formulations can also be administered by two or more routes, where the delivery methods are essentially simultaneous or they may be essentially sequential with little or no temporal overlap in the times at which the composition is administered to the subject.

Suitable regimes for initial administration and further doses or for sequential administrations also are variable, may include an initial administration followed by subsequent administrations, but nonetheless, may be ascertained by the skilled artisan from this disclosure, the documents cited herein, and the knowledge in the art.

A pharmaceutical composition of the present invention may also comprise one or more growth factors or cytokines (e.g., angiogenic cytokines) that promote the survival or engraftment of transplanted cells, promote angiogenesis, modulate the composition of extracellular or interstitial matrix, and/or recruit other cell types to the site of transplantation.

In some cases, the therapeutic agent may be optionally administered in combination with one or more additional active agents. Such active agents include rapamycin, analogs of rapamycin and paclitaxel. Any suitable combination of such active agents is also contemplated. When administered in combination with one or more active agents, the therapeutic agent can be administered either simultaneously or sequentially with other active agents. For example, victims of intimal hyperplasia may simultaneously receive the therapeutic agent and rapamycin, analogs of rapamycin, or paclitaxel for a length of time or according to a dosage regimen sufficient to support recovery and to treat, alleviate, or lessen the severity of the intimal hyperplasia.

In some embodiments, RepSox is administered to a subject in need thereof using an infusion, topical application, surgical transplantation, or implantation. In an exemplary embodiment, administration is systemic. In such cases, RepSox can be provided to a subject in need thereof in a pharmaceutical composition adapted for intravenous administration to subjects. Typically, compositions for intravenous administration are solutions in sterile isotonic aqueous buffer. The use of such buffers and diluents is well known in the art. Where necessary, the composition may also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. In some cases, compositions comprising the therapeutic agent are cryopreserved prior to administration.

In some embodiments, a treatment method of the present invention can comprise transplanting the SMCs into the recipient subject. This is generally effected using methods well known in the art, and usually involves directly injecting or otherwise introducing SMCs into the subject using clinical tools known to those skilled in the art (e.g., U.S. Pat. Nos. 6,447,765; 6,383,481; 6,143,292; and 6,326,198). Cells can be injected into an infusion bag (e.g., Fenwal infusion bag (Fenwal, Inc.)) using sterile syringes or other sterile transfer mechanisms. The cells can then be immediately infused via IV administration over a period of time, such as 15 minutes, into a free flow IV line into the patient. In some embodiments, additional reagents such as buffers or salts are provided to the recipient subject concurrently with the cells.

Therapeutically effective amounts of the therapeutic agent are administered to a subject in need thereof. An effective dose or amount is an amount sufficient to effect a beneficial or desired clinical result. With regard to methods of the present invention, the effective dose or amount, which can be administered in one or more administrations, is the amount of the therapeutic agent sufficient to elicit a therapeutic effect in a subject to whom the cells are administered. In some embodiments, the therapeutic agent is RepSox and an effective dose is about 25 mg to about 500 mg (i.e., about 25, 50, 100, 200, 250, 300, 350, 400, 450, or 500 mg) per $cm^2$ of lesion size delivered locally to the site of the lesion of the recipient. In some embodiments, the therapeutic agent is SMCs and an effective dose is about $1\times10^6$ cells/kilogram to about $1\times10^8$ cells/kilogram (i.e., about $1\times10^6$, $2\times10^6$, $5\times10^6$, $1\times10^7$, $2\times10^7$, $5\times10^7$, $1\times10^8$ cells/kilogram) of body weight of the recipient. Effective amounts will be affected by various factors which modify the action of the therapeutic agent upon administration and the subject's biological response to the therapeutic agent, e.g., severity of intimal hyperplasia, type of damaged tissue, the patient's age, sex, and diet, time of administration, and other clinical factors.

Therapeutically effective amounts for administration to a human subject can be determined in animal tests and any art-accepted methods for scaling an amount determined to be effective for an animal for human administration. For example, an amount can be initially measured to be effective in an animal model (e.g., to achieve a beneficial or desired clinical result). The amount obtained from the animal model can be used in formulating an effective amount for humans by using conversion factors known in the art. The effective amount obtained in one animal model can also be converted for another animal by using suitable conversion factors such as, for example, body surface area factors.

It is to be understood that, for any particular subject, specific dosage regimes should be adjusted over time according to the individual need and the professional judgment of the person administering or supervising the administration of the therapeutic agent. For example, a therapeutic agent dosage for a particular subject which intimal hyperplasia can be increased if the lower dose does not elicit a detectable or sufficient improvement. Conversely, the dosage can be decreased if the intimal hyperplasia is treated or eliminated.

In some cases, therapeutically effective amounts of the therapeutic agent can be determined by, for example, measuring the effects of a therapeutic in a subject by incrementally increasing the dosage until the desired symptomatic relief level is achieved. A continuing or repeated dose regimen can also be used to achieve or maintain the desired result. Any other techniques known in the art can be used as well in determining the effective amount range. Of course, the specific effective amount will vary with such factors as the particular disease state being treated, the physical condition of the subject, the type of animal being treated, the duration of the treatment, and the nature of any concurrent therapy.

After administering the cells into the subject, the effect of the treatment method may be evaluated, if desired, using any appropriate method known to practitioners in the art. The treatment may be repeated as needed or required. For example, for methods of treating intimal hyperplasia in a subject, positive or negative changes in the subject's echocardiography during or following treatment may be determined by any measure known to those of skill in the art including, without limitation, measuring left ventricular ejection fraction.

In some cases, a substantially pure population of smooth muscle cells is obtained using a pluripotent cell (e.g., induced pluripotent stem cell) of the subject in need of treatment. However, a substantially pure population of smooth muscle cells also can be obtained using pluripotent stem cells of, preferably, a syngeneic or allogeneic donor. Less preferably, a xenogeneic donor is used. As used herein, the term "allogeneic" refers to something that is genetically different although belonging to or obtained from the same species (e.g., allogeneic tissue grafts or organ transplants).

Compositions

In a further aspect, provided herein are isolated populations of SMCs obtained according to the methods provided herein. Such cell populations are useful for various in vitro and in vivo applications such as engineering new blood vessels, smooth muscle cell transplantation, vascularization of other engineered tissues, and vascular disease modeling. The disclosed methods facilitate production and use of SMC populations.

More specifically, human iPS cell-derived SMCs allow modeling of drug responses in tissue constructs that recapitulate arterial tissue in an individual having, for example, a particular disease. Even the safest drugs may cause adverse reactions in certain individuals having a specific genetic background or environmental history. Accordingly, iPS cell-derived SMCs obtained according to methods of the present invention from individuals having known susceptibilities or resistances to various drugs or diseases will be useful in identifying genetic factors and epigenetic influences that contribute to variable drug responses.

Subject-specific somatic cells for reprogramming into induced pluripotent stem cells can be obtained or isolated from a target tissue of interest by biopsy or other tissue sampling methods. In some cases, subject-specific cells are manipulated in vitro prior to use in accord with the invention. For example, subject-specific cells can be expanded, differentiated, genetically modified, contacted to polypeptides, nucleic acids, or other factors, cryo-preserved, or otherwise modified prior to use.

The invention also provides a kit for differentiating human pluripotent stem cells into SMCs, comprising (i) a first culture medium sufficient for differentiation of human pluripotent stem cells into mesodermal cells; (ii) a second culture medium sufficient for differentiation of mesodermal cells into MEOX1 expressing cells; (iii) a third culture medium sufficient for suppressing MEOX1 expression; (iv)

a fourth culture medium sufficient to induce SMC progenitors; (v) a fifth culture medium comprising an MYH11 agonist sufficient to differentiate SMC progenitors into contractile smooth muscle cells; and (iii) instructions describing a method for differentiating human pluripotent stem cells into contractile smooth muscle cells, the method employing the first, second, third, fourth, and fifth culture media. In some embodiments, the MYH11 agonist of the fifth culture medium is RepSox.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein.

In the specification and in the claims, the terms "including" and "comprising" are open-ended terms and should be interpreted to mean "including, but not limited to . . . " These terms encompass the more restrictive terms "consisting essentially of" and "consisting of." As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising," "including," "characterized by," and "having" can be used interchangeably.

As used herein, "a medium consisting essentially of" means a medium that contains the specified ingredients and those that do not materially affect its basic characteristics.

As used herein, "effective amount" means an amount of an agent sufficient to evoke a specified cellular effect according to the present invention.

As used herein, "about" means within 5% of a stated concentration range, density, temperature, or time frame.

The invention will be more fully understood upon consideration of the following non-limiting Examples. It is specifically contemplated that the methods disclosed are suited for pluripotent stem cells generally.

Example 1

The embodiment described here demonstrates the inventor's recognition that small molecule RepSox causes cells to maintain a contractile phenotype in vitro and in vivo. Also demonstrated are exemplary embodiments of the differentiation of human pluripotent stem cells into contractile smooth muscle cells using RepSox.

The embodiment described here uses high-throughput screening to identify small molecules that can promote contractile SMC differentiation. Since normal vascular differentiation and the dedifferentiation observed in vascular disease share common pathways, this screening strategy using human pluripotent stem cell-SMC cell differentiation could identify drug candidates that prevent restenosis caused by intimal hyperplasia.

The selection of reporter gene is critical for achieving an efficient screening (Hughes et al., 2011). MYH11 is a highly specific protein for SMCs and is a marker for the mature contractile phenotype (Owens et al., 2004). The mutation or reduced expression of MYH11 is associated with vascular diseases (Owens et al., 2004; Pannu et al., 2007). Thus, using CRISPR-Cas9 technology (Cong et al., 2013; Hou et al., 2013; Mali et al., 2013), we generated a MYH11-NLuc-Tom human ES cell reporter cell line for use in a high-throughput screening. Using this reporter cell line in a high-throughput screening of 4804 small molecules, we identified RepSox as a new potent small molecule for promoting contractile SMC differentiation from human pluripotent stem cells. SMCs generated by RepSox (RepSox-SMCs) demonstrated more contractile phenotype compared to P-SMCs (SMCs induced by PDGF-BB), T-SMCs (SMCs induced by TGF-β1), and PT-SMCs (SMCs induced by both TGF-β1 and PDGF-BB). We further demonstrated that RepSox promoted synthetic to contractile phenotypic switching of primary human aortic SMCs (AoSMCs) in vitro and inhibited intimal hyperplasia in vivo. Finally, Rep-Sox SMCs increased survival in a mouse hind limb ischemia model, suggesting that these SMCs could have therapeutic value by themselves.

Methods

Gene targeting on the H1 ES cells—The 5'- and 3'-homology arms of MYH11 targeting vector were synthesized by IDT (gBlock) and cloned into an NLuc and Tom containing vector. NLuc and Tom were inserted into the first exon of MYH11. To achieve the best electroporation efficiency, human ES cells (H1) were passaged with EDTA (1:4 split) and cultured to reach 80-90% confluency two days before the experiment. On the day of the experiment, ES cells were dissociated by ACCUTASE™, washed once with E8 medium, and resuspended at densities of $5 \times 10^6$ cells/mL in E8 medium with 10 mM Hepes buffer (pH 7.2-7.5) (Life Technologies). For electroporation, 400 µL of cell suspension, 7.5 µg gRNA plasmid, 7.5 µg spCas9 plasmid, and 10 linearized DNA template plasmid were mixed in a 4-mm cuvette (Bio-Rad) and immediately electroporated with a Bio-Rad Gene Pulser. Electroporation parameters were set at 250 V, 500 and infinite resistance. Cells were then plated on a MATRIGEL™-coated plate in E8 medium (10 µM Y27632 was added for the first day). Geneticin (100 µg/ml) was added to the medium when cells reached 20% confluency (usually 3-4 days after electroporation) and the treatment lasted for five days. Surviving colonies were picked 4-6 days after drug selection and expanded in E8 medium.

Karyotyping—Karyotyping was performed by the WiCell Research Institute.

Southern Blot—PCR DIG Probe Synthesis Kit (Roche, Cat #11 636 090 910) was used for synthesis of the probe. The southern blot was performed following the DIG Application Manual for Filter Hybridization from Roche.

High-throughput screening—The MYH11-Nluc-2A-Tom reporter human ES cell line was differentiated into mesoderm by using E8BAC (E8 medium supplemented with 5 ng/mL BMP4, 25 ng/mL Activin A, and 1 µM CHIR99021) medium for two days. The cells were treated with 50 ng/ml FGF2 and 20 ng/ml BMP4 for another two days. The cells were passaged at day 4 and seeded on the 96-well plate for screening ($2 \times 10^6$ cells/plate). The compounds were added from day 4-14. The Luciferase substrate (1000× dilution) (Nano-Glo Luciferase Assay system, Promega) was added to the medium for 15 min and luminescence was measured. An increase in luminescence indicates increased MYH11 expression, which is an indicator of the contractile smooth muscle cell phenotype. The Thomson custom stem cell Modulator 1, GSK-kinase inhibitor library, SellekChem Kinase inhibitor library, Analyticon NATx library, Prestwick Chemical Library, GlaxoSmithKline Protein Kinase Inhibitors, and part of Enamine Representative Diversity library were used for screening.

Optimized smooth muscle cell differentiation—Human pluripotent stem cell cells (H1) were cultured in E8 medium on a MATRIGEL™-coated plate. To achieve the best differentiation results, ES cells were split using EDTA at 1:4 ratios two days before the differentiation. The cells reached 80-90% confluency two days later. At the day of the differentiation, ES cells were dissociated by ACCUTASE™ (Invitrogen) for 3-5 min at 37° C. The cells were plated on a MATRIGEL™-coated plate at 1:4 ratios (1×105 cells/cm2). The cells were cultured in E8BAC medium (E8 medium supplemented with 5 ng/mL BMP4, 25 ng/mL Activin A, and 1 µM CHIR99021) for 36 hours. An increased CHIR99021 concentration of 3 µM decreased cell proliferation at 36 hours but increased MYH11 expression. At 36 hours, the cells were passaged and seeded on a new MATRIGEL™-coated plate (1.6×10$^4$ cells/cm2). The low cell density is critical for the differentiation. A cell density of 1.0-4.0×10$^4$ cells/cm2 for different cell lines can be tested, such that 100% cell confluence will be achieved at day 6, which gives rise to the best differentiation efficiency. The cells were treated with E6T medium (E8 medium minus FGF2 but still containing 1.7 ng/ml TGF-β1) for 18 hours to induce the transient and medium level expression of MEOX1. E5F medium (E8 medium minus insulin and TGF-β1, but still containing 100 ng/ml FGF2) was used to suppress MEOX1 expression for another 5 days (days 3-8). Next, the cells were treated with E6FVR medium (E6 medium with 100 ng/ml FGF2, 50 ng/ml VEGFA, and 5 µM RESV, a NOTCH agonist) to induce SMC progenitors from day 8-12. E6R (E6 medium+5 µM RESV) medium supplemented with RepSox (25 µM), was then used to further mature SMCs from day 12 to 24. Cells were split (1×10$^5$ cells/cm2) at day 16 and further differentiated until day 24. The cells can be cryopreserved at day 16 or day 24. For P-SMCs, T-SMCs, and PT-SMCs, RepSox was replaced by PDGF-BB (10 ng/ml), TGF-β1 (1.7 ng/ml), or combination of PDGF-BB and TGF-β1, respectively, from day 12 to 24. From day 0-4: medium was changed every day. From day 2-24: medium was changed every other day. For day 1 and day 8-24, 1.5×volumes of medium, compared to the normal volume used in the well, were used. For example, in a 12 well plate, 1 ml/well is normally used, therefore 1.5 ml/well would be used in this protocol.

RepSox-SMCs, P-SMCs, T-SMCs and PT-SMCs were maintained in E6R medium supplemented with RepSox, PDGF-BB, TGF-β1, or PDGF-BB and TGF-β1, respectively. AoSMCs were maintained in SmGM2 (Lonza) medium.

In a first alternative method, RESV can be withdrawn from the medium from day 8-12.

In a second alternative method, FVR medium can be used from day 8-10 and then changed to E6R medium supplemented with RepSox from day 10-24.

Cell proliferation assay—Smooth muscle cells were seeded on a MATRIGEL™-coated plate (3×10$^4$ cells/cm2). In the next day, 100 µM EdU was added the medium for 3 hours and cell proliferation was measured by Click-it EdU Kit (ThermoFisher, cat #C10425) according to the manufacturer's instructions.

Cell migration assay—Cell suspension (70 µl/well, 5×10$^5$ cells/ml) was seeded in the migration insert (culture-insert 2 well in µ-dish 35 mm, ibidi). In the next, inserts were removed and washed with fresh medium twice. Cells were imaged at the indicated time point.

Cell contraction assay—Smooth muscle cells were seeded on a MATRIGEL™-coated plate (1×10$^4$ cells/cm2). In the next day, 100 µM carbachol was added to the medium for 30 min. The cells were imaged before and after carbachol treatment. To facilitate the calculation of the cell surface change, the cells were stained with 5 µM CMFDA (green fluorescence) for 30 min before carbachol treatment. The cell surface change was measured by ImageJ.

Kidney capsule—The experiments were performed under approval from the Animal Care and Use Committee of the University of Wisconsin School of Medicine and Public Health and the Health Sciences Institutional Review Board. NOD-SCID mice were used for the experiments as previously described (Brown et al., 2018). The tissues were collected 4 weeks after surgery.

Hind limb ischemia model—The experiments were performed under approval from UW-Madison Cardiovascular Physiology Core Facility IRB. The Hind limb ischemia model was generated as previously described (Couffinhal et al., 1998). Briefly, 10-12 weeks old female athymic nude mice (Crl:NU(NCr)-Foxn1nu, Charles River Laboratories, Chicago, Illinois) were used. To mimic human conditions, 10-12 weeks old instead of 4-6 weeks old mice were used as the older mice recover slower. The common iliac artery was ligated in the abdominal cavity and just caudal to the inguinal ligament, the femoral artery was ligated in two locations and removed. The mice were randomly assigned into 2 groups right after surgery and injected cells or PBS medium. Cells (1×10$^7$ cells per mouse) were suspended in 300 µl PBS medium and injected intramuscularly into six sites of the gracilis muscle in the ischemic leg. Surgery was performed on seven to eight mice per day.

Rat carotid artery balloon injury model and periadventitial delivery—This animal study was conducted with approval from the UW-Madison Department of Surgery Animal Care and Use Committee. Briefly, 2 mg (2 animals/group) or 10 mg (3 animals/group) of RepSox (or DMSO) dissolved in Regel (Tri-block gel) (Regel tri-block gel is described in Chen et al. "Unimolecular Micelle-Based Hybrid System for Perivascular Drug Delivery Produces Long-Term Efficacy for Neointima Attenuation in Rats," Biomacromolecules, 2017 Jun. 14. doi: 10.1021/acs.biomac.7b00617) was applied to the outside of the injured artery segment immediately after balloon injury of the rat carotid artery. Two weeks post-surgery, arteries were collected and sectioned. The ratio of intima area versus media area and lumen area were measured by Image J.

Results

High-throughput screening directs contractile smooth muscle cell differentiation—The construction of the MYH11-NLuc-tdTomato human ES cell reporter line generated by CRISPR/Cas9 technology is described in FIGS. 6A-6H. The reporter cell line was differentiated into mesoderm in E8BAC medium (Zhang et al., 2017) for two days and treated with FGF2 and BMP4 to further mature mesoderm for another two days. The cells were then passaged into a 96-well plate and exposed to small molecules for 10 days using a customized robotic workstation (FIG. 1A). The workstation was designed through collaboration with TECAN, which enables us to perform the automatic high-throughput screening at specific time point and in long-term. The medium were changed every other day and the small molecules were added during the feeding. Among the 4804 small molecules tested, 42 of them significantly improved contractile SMC differentiation, as evident by the increased MYH11 promoter-driven luciferase activity (Table 2, FIGS. 1B-1C). We then validated these hits and optimized their concentration. Among them, RepSox was the most effective at promoting MYH11 expression and was used for further optimizing contractile SMC differentiation (FIG. 1C).

Figures 7A, 7B, 7C, 7D, 7E, 7F, 7G:
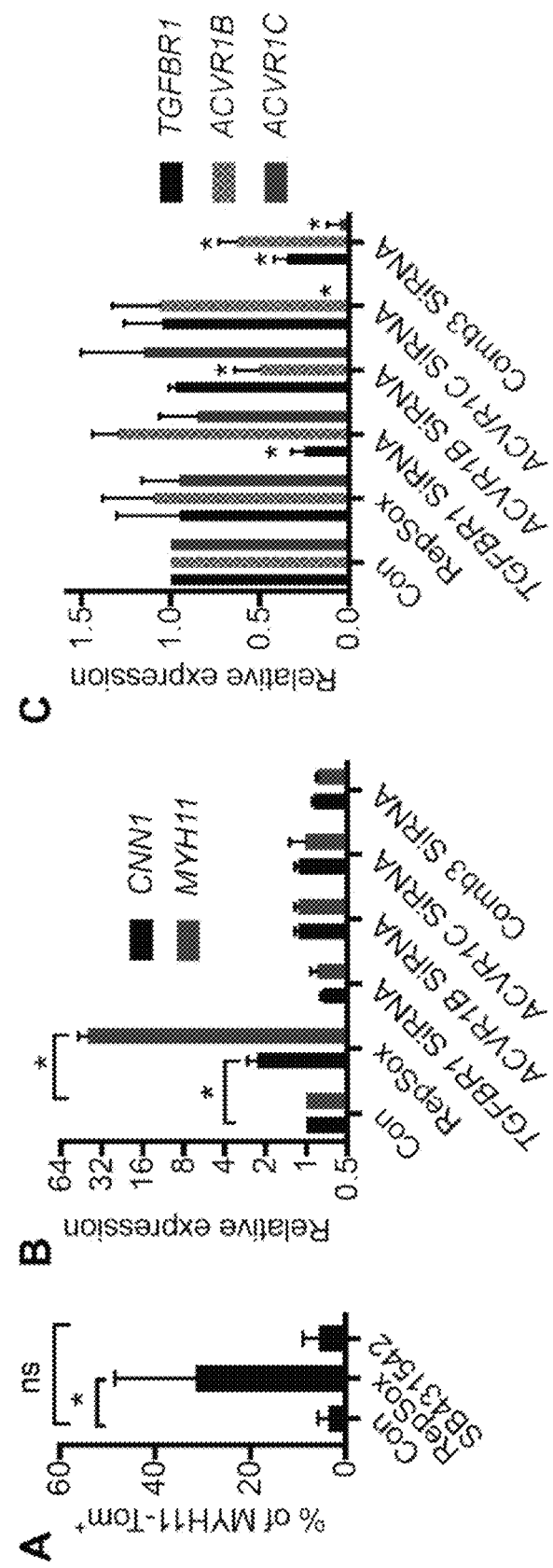
FIGS. 7A-7G show the target of RepSox.
Figures 7A, 7B, 7C, 7D, 7E, 7F, 7G:
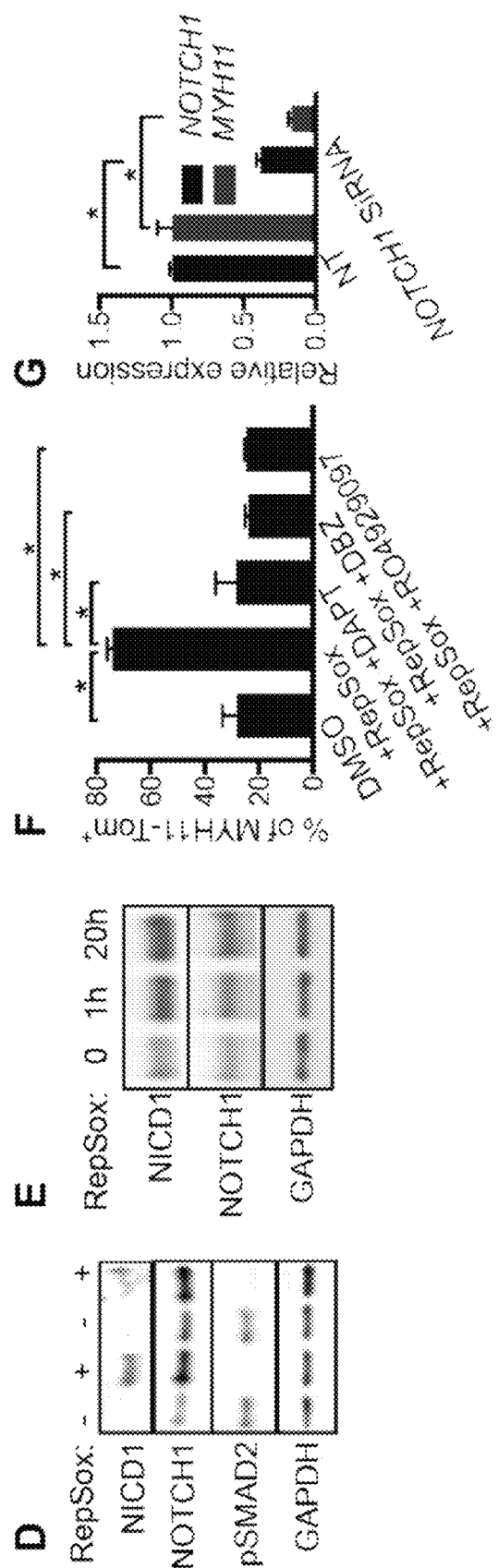
Figures 8A, 8B, 8C, 8D, 8E, 8F:
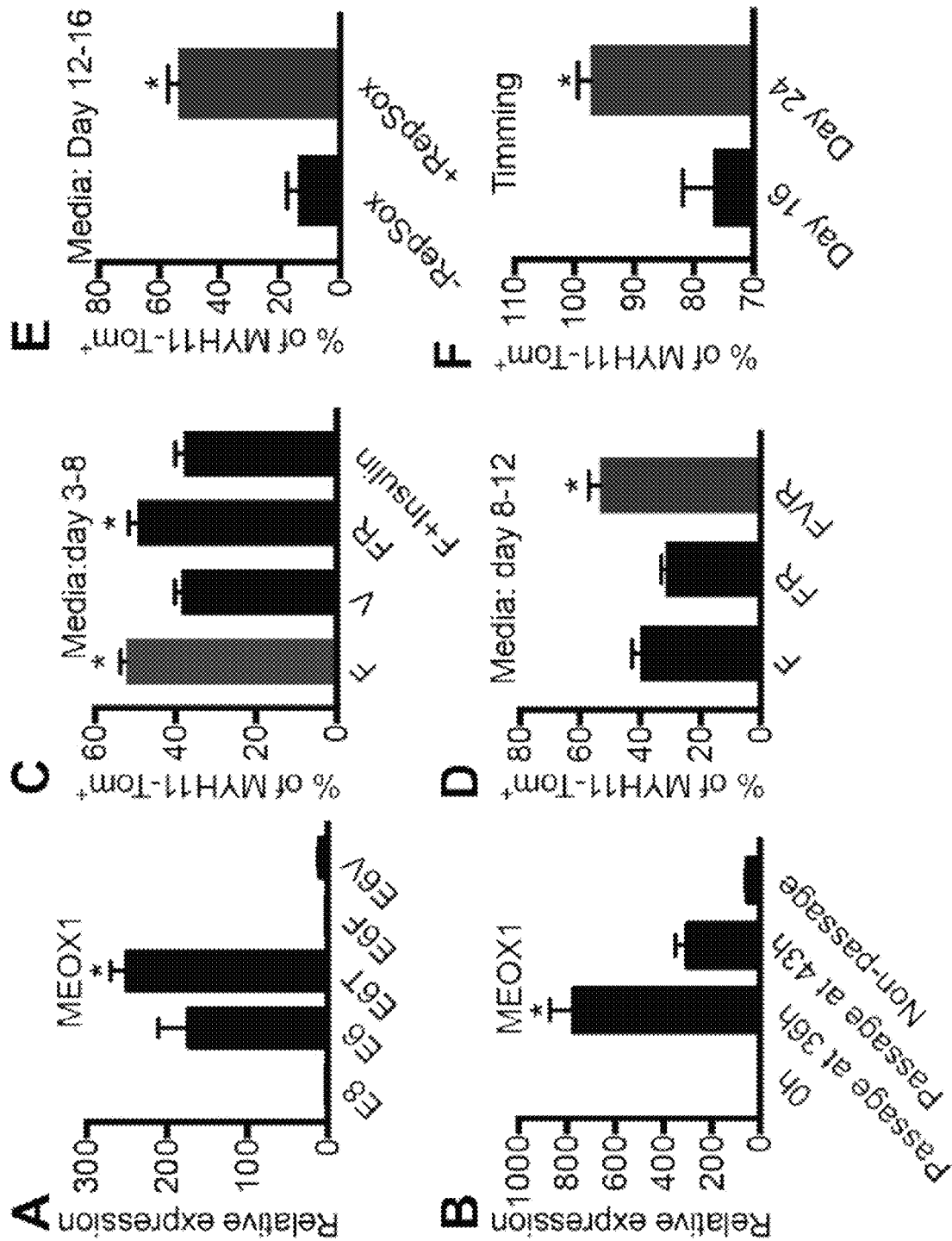
FIGS. 8A-8F show optimization of SMC differentiation in xeno-free medium.

RepSox was previously described as a TGF-β3 signaling inhibitor (Ichida et al., 2009). However, inhibition or knockdown of TGF-β3 receptors failed to increase MYH11 expression (FIGS. 7A-7C). Instead, our results revealed that RepSox enhanced full-length NOTCH1 and its intracellular domain (NICD, activated form) expression (FIG. 7D). The increased NOTCH signaling could be detected after 1 hour of RepSox treatment (FIG. 7E), suggesting that NOTCH signaling could be a direct target of RepSox. In addition, inhibition of NOTCH signaling by DAPT, DBZ, or RO4929097 abolished the effect of RepSox in the improvement of MYH11-Tom+ cell differentiation (FIG. 7F). Consistently, knockdown of NOTCH1 suppressed MYH11 expression (FIG. 7G). These data suggested that RepSox modulated NOTCH pathways to promote contractile SMC differentiation.

TABLE 2

Small molecule hits from high-throughput screen which improved contractile SMC differentiation, as evident by the increased MYH11 promoter-driven luciferase activity.

| Library | Compound catalog No. | Trade name | SMILES* |
|---|---|---|---|
| Analyticon NATx Library | NAT16-352622 | No trade name | CCNC(=O)N[C@H]1C[C@@H](C=C1)C1=C(O)N(N=C1)C1=CC=C(C=C1)CC)C |
| Analyticon NATx Library | NAT15-330204 | No trade name | COC(=O)[C@@H]1CC2=C(NC3=C2C=CC=C3)[C@H]2C[C@H]1C[C@@H](N12)C1=CC=CC=C1)NCC1=CC=CC=C1 |
| Analyticon NATx Library | NAT13-338612 | No trade name | COC1=CC=C(=C1OC)C1=NN(C)C=C1)[C@H]1CO[C@@H]2C[C@@H]2CN[C@@H]2CNC(=O)NC1=CC=CC=C1)C#N |
| Analyticon NATx Library | NAT6-298378 | No trade name | O=C(N[C@H]1CO[C@@H]2[C@@H](CO[C@H]12)N1N=NN=C1OC1=CC=C2OCOC2=C1)NC1=CC=CC2=CC=CC=C12 |
| Analyticon NATx Library | NAT18-381960 | No trade name | CN1[C@H](C[C@H]1C1=NC(=NO1)C1=CC=C(C1)C=1)NS(=O)(=O)C1=CC=C(C1)C#N |
| Analyticon NATx Library | NAT18-355551 | No trade name | CN1[C@H](C[C@H]1C1=NC(=NO1)C1=CC=C(C1)C=1)NS(=O)(=O)C1=CC(F)=CC=C1 |
| Analyticon NATx Library | NAT6-324295 | No trade name | FC1=CC(=CC=C1)C1=CC=NC(N[C@H]2CO[C@@H]3C[C@@H]3C[C@@H](CO[C@@H]23)NC(=O)NC2=CC(=CC=C2)C#N)=N1 |
| Analyticon NATx Library | NAT23-390920 | No trade name | COC1=CC=C(CN2C(C@@H]2CNC(=O)[C@@H]2CNC3=NC=CN3)N2O)C=C1 |
| Analyticon NATx Library | NAT31-470153 | No trade name | COC1=CC=C(CN2[C@@H]3CN(C[C@@H]3OCC2=O)C(=O)CC2=CNC3=C2C=CC=C3)C=C1 |
| Analyticon NATx Library | NAT37-510679 | No trade name | FC1=CC=C(CN2[C@@H]3CN(C[C@@H]3OCC2=O)C(=O)CC2=CNC3=C2C=CC=C3)C=C1 |
| Enamine 2011 Representative Diversity Library | T0520-3169 | No trade name | CC1=NN(C2=C1C(N1C(=CC3=C1C=CC=C3)=N2)C1=C(C1)C=CC=C1F)C1=CC=C(C1)C=C1 |
| Enamine 2011 Representative Diversity Library | T5341423 | No trade name | CC(C)CCN1C(=O)C2=C(C=C(C=C2)C(=O)OCC(=O)C2=C(N)C(CC(=O)NC(C=O))C2=O)C1=O |
| Enamine 2011 Representative Diversity Library | T5342130 | No trade name | CN(C1CCCC2=C1C=CC=C2)C1=C2C=C(SC2=NC=N1)C1=CC=CC=C1 |
| Enamine 2011 Representative Diversity Library | T5343121 | No trade name | NS(=O)(=O)C1=CC=C(C=C1)N1CCN(CC1)S(=O)(=O)C1=CC=CS1)[N+]([O-])=O |
| Enamine 2011 Representative Diversity Library | T5216652 | No trade name | OC1=C(O)C=C2C(COC(=O)C3=NN(C4=CC=CC=C4)C(=O)C4=C3C=CC=C4)=CC(=O)OC2=C1 |
| GlaxoSmithKline Protein Kinase Inhibitors | GSK182497A | No trade name | CN(O)C(=O)OC1CC(NC1)C#CC2=CC3=C(S2)C(=NC=N3)NC4=CC=C(=CC4)OCC5=CC(=CC=C5)F)C1 |
| GlaxoSmithKline Protein Kinase Inhibitors | GW282449A | No trade name | COC1=C(C=C2C(=C1)C(=NC=N2)NC3=CC4=C(C=C3)N(N=C4)CC5=CC=CC=C5)OC.C1 |
| GlaxoSmithKline Protein Kinase Inhibitors | GW607049C | No trade name | COC(=O)NC1=NC2=C(N1)C=C(C=C2)SC3=CC=C(C=C3)NC(=O)NC4=CC(=CC=C4)C(F)(F)F |
| GlaxoSmithKline Protein Kinase Inhibitors | GSK1023156A | No trade name | NC(=O)c1sc(cc10Cc2ccccc2Br)n3cnc4ccccc34 |
| Prestwick Chemical Library | Prestw-13 | Hydroflumethiazide | FC(F)(F)c1c(cc2c(c1)NCNS2(=O)=O)S(=O)(=O)N |
| Prestwick Chemical Library | Prestw-14 | Sulfacetamide sodic hydrate | [N-]{S(=O)(=O)c1ccc(cc1)N}C(=O)C |
| Prestwick Chemical Library | Prestw-20 | Minoxidil | [n+]1(c(nc(cc1N)N2CCCCC2)N)[O-] |
| Prestwick Chemical Library | Prestw-21 | Sulfaphenazole | S(=O)(=O)(N(N)C1=CC=NN1 c2ccccc2)c3ccc(cc3)N |
| Prestwick Chemical Library | Prestw-173 | Tranylcypromine hydrochloride | NC1C(C1)c2ccccc2 |
| Prestwick Chemical Library | Prestw-442 | Fusaric acid | n1c(ccc(c1)CCCC)C(=O)O |
| Prestwick Chemical Library | Prestw-666 | Nisoldipine | COC(=O)C1=C(N)C(=C(C1)NC2=C(C1C1=CC=CC=C1[N+]([O-])=O)C(=O)OC(C)C |
| Selleck Kinase Inhibitors | S1026 | Imatinib Mesylate | C1=CC=C(C(=C1)NC2=NC=CC(=N2)C3=CC=CN=C3)NC(=O)C4(=CC=C(C=C4)CN5CCN(CC5)C).OS(C(=O)=O |
| Selleck Kinase Inhibitors | S1040 | Sorafenib (Nexavar) | C1=CC=C(C1C(F)(F)F)NC(NC2=CC=C(C=C2)OC3=CC=NC(=C3)C(N)=O)=O)C1.C4=CC=CC=C4S(O)(=O)=O)C |
| Selleck Kinase Inhibitors | S1102 | U0126-EtOH | C1=CC=C(C(=C1)SC(N)=C(C(=C(SC2=C(C=C2N)N)C#N)C#N),CCO |
| Selleck Kinase Inhibitors | S1220 | OSI-930 | C1=CC=C(C=C1)C(=N2)CNC3=C(SC=C3)CNC4=CC=C(C=C4)OC(F)(F)F)=O |

TABLE 2-continued

Small molecule hits from high-throughput screen which improved contractile SMC differentiation, as evident by the increased MYH11 promoter-driven luciferase activity.

| Library | Compound catalog No. | Trade name | SMILES* |
|---|---|---|---|
| Selleck Kinase Inhibitors | S2634 | DCC-2036 (Rebastinib) | C1(=C(C=C(C=C1)OC2=CC(=NC=C2)(NC)=O)F)NC(NC3N(N=C(C=3)C)(C)C)C4=CC5=C(C=C4)N=CC=C5)=O |
| Selleck Kinase Inhibitors | S2220 | SB590885 | N1C(=C(NC=1C2=CC=C(C=C2)OCCN(C)C)C3=CC=C4C(=C3)CCC4=N/O)C5=CC=NC=C5 |
| Selleck Kinase Inhibitors | S2386 | Indirubin | C1=CC=C2C(=C1)NC(C/2=C3NC4=C(C3=O)C=CC=C4)=O |
| Thomson Custom Stem Cell Modulator 1 | 04-0001 | RG108 | O=C1N([C@H](C(O)=O)CC2=CNC3=C2C=CC=C3)C(C4=C1C=CC=C4)=O |
| Thomson Custom Stem Cell Modulator 1 | 04-0021 | All-Trans Retinoic Acid | O=C(O)C=C(C=C=C(C=C=C1C1=C(CCCC1(C)C)C)C |
| Thomson Custom Stem Cell Modulator 1 | 3742 | RepSox (SJN 2511) | CC1=NC(C2=NNC=C2C3=NC4=CC=CN=C4C=C3)=CC=C1 |
| Thomson Custom Stem Cell Modulator 1 | 2721 | ABS 205 | CCCC(CC#C)C(=O)O |
| Thomson Custom Stem Cell Modulator 1 | 1769 | Flurbiprofen | CC(C1=CC(=C(C=C1)C2=CC=CC=C2)F)C(=O)O |
| Thomson Custom Stem Cell Modulator 1 | C7482-5s | Sitagliptin | Fc1cc(cF)cc1F)C[C@@H](N)CC(=O)N3Cc2nnc(n2CC3)C(F)(F)F |
| Thomson Custom Stem Cell Modulator 1 | C2135 | BI-1356 | CC#CCN1C2=C(N=C1N3CCC[C@H](C3)N)N(C(=O)N(C2=O)CC4=NC5=CC=CC=C5C(=N4)C)C |
| Thomson Custom Stem Cell Modulator 1 | 04-0029 | Y27632 | O=C([C@H]1CC[C@@]([C@H](C@@H]2[C@@H](C@@H](C@@H])(C@@H](N)C)(H])CC1)NC2=CC=NC=C2 |
| Thomson Custom Stem Cell Modulator 1 | 04-0025 | Forskolin | CC(=O)O[C@H]1[C@H]([C@@H]2[C@]([C@H](CCC2(C)C)O)([C@@]3[C@]1(O)[C@@](CC3=O)(C=C)C)C)O |

*SMILES: simplified molecular-input line-entry system

Note:
All the compounds are publicly available

Figures 2A, 2B, 2C, 2D, 2E, 2F:
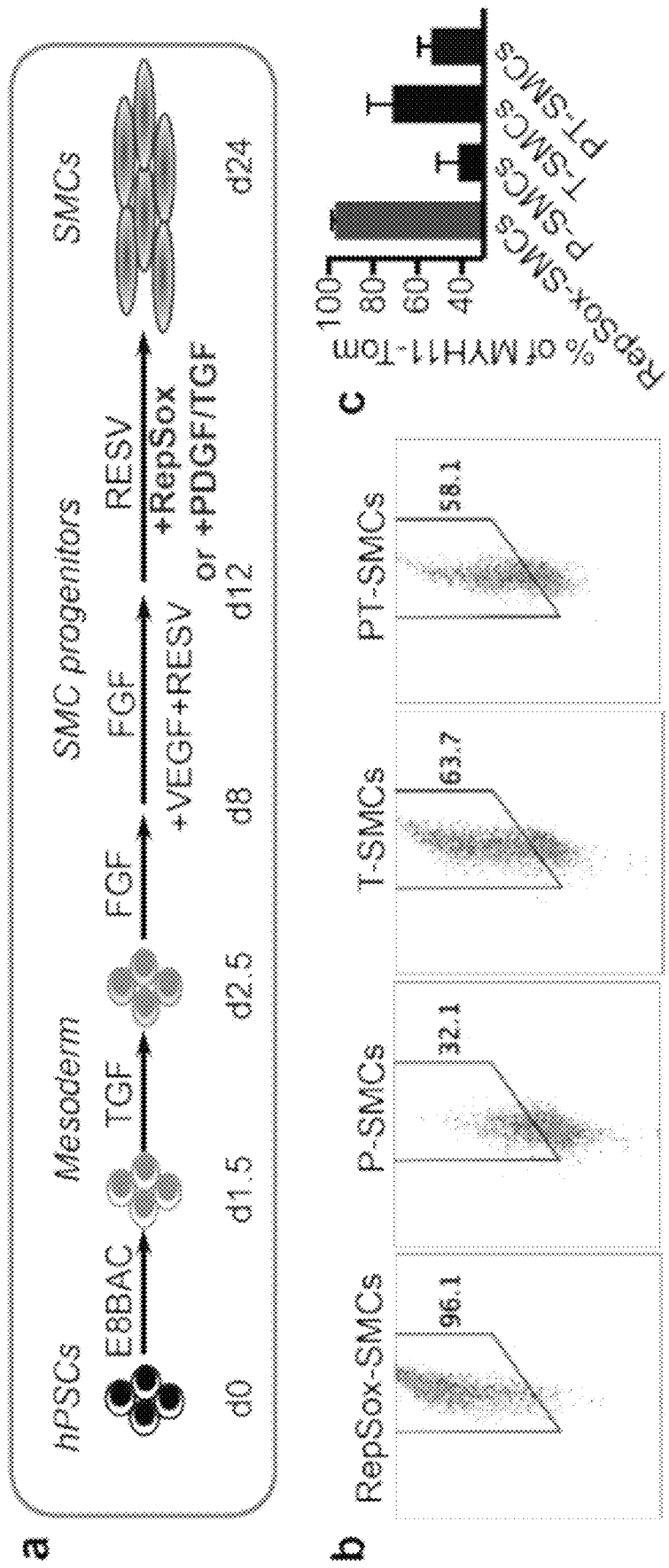
FIGS. 2A-2F show a schematic of differentiation and molecular characterization of smooth muscle cells.
Figures 2A, 2B, 2C, 2D, 2E, 2F:
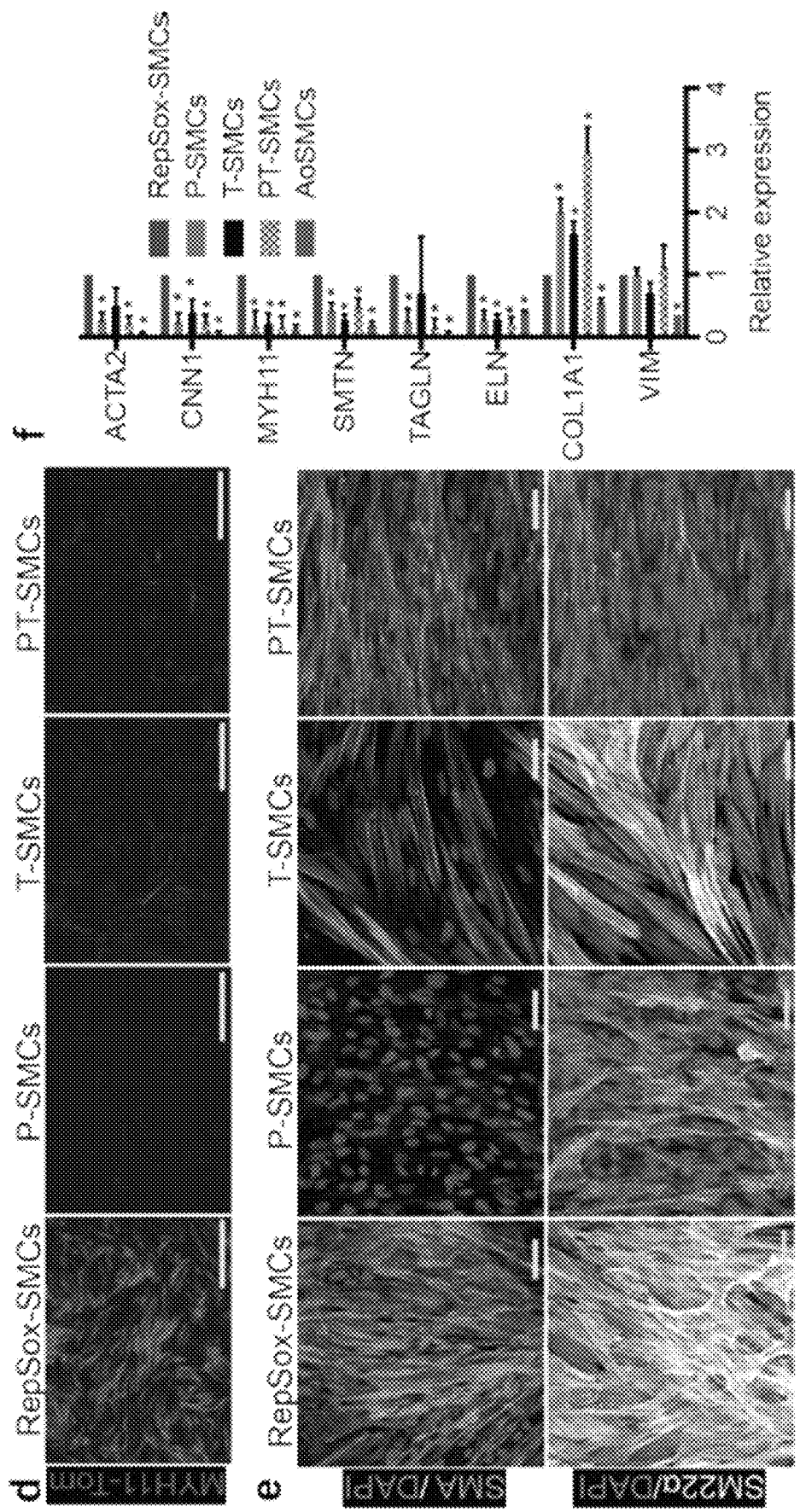
Figure 9A:
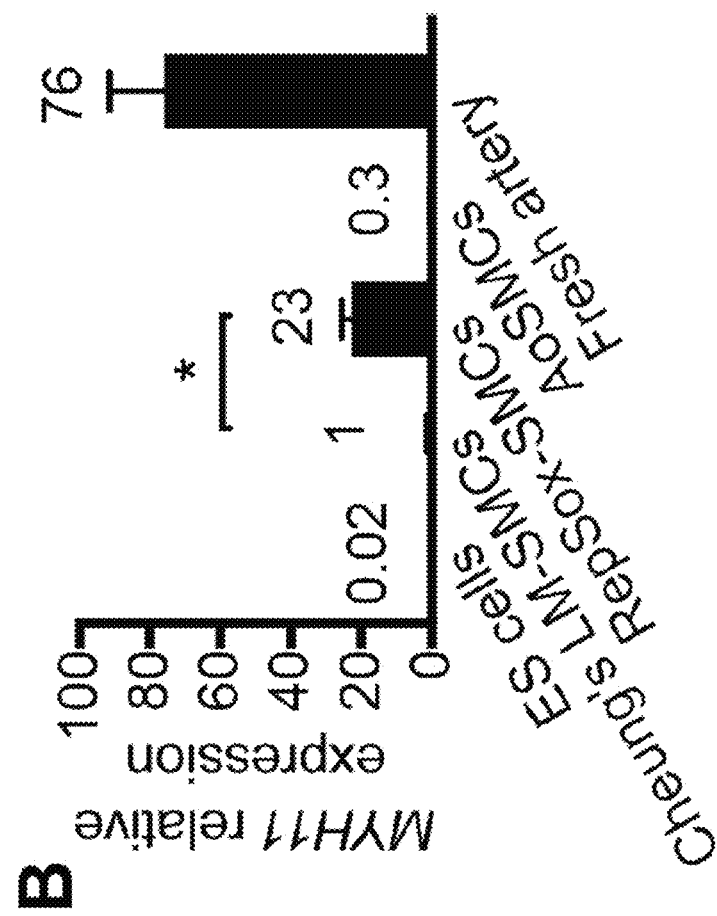
FIGS. 9A-9B show a comparison of MYH11 expression in RepSox-SMCs and Cheung's LM-SMCs.
Figure 9B:
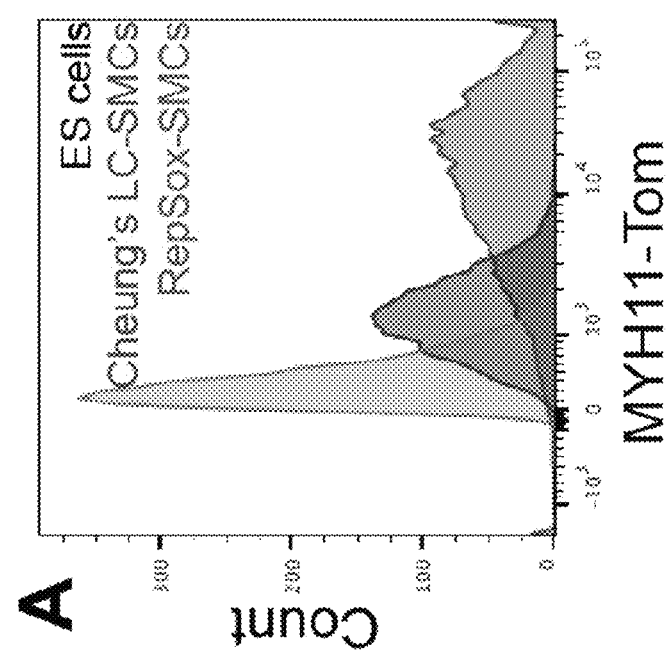

Next, we optimized the differentiation protocol and compared RepSox-SMCs, P-SMCs, T-SMCs, and PT-SMCs (FIG. 2A). RepSox induced a higher efficiency of SMC differentiation (>95% MYH11-tdTomato+) than the PDGF-BB and TGF-β1 protocols (FIGS. 2B and 2D), and the MYH11-tdTomato expression level in individual cells was higher in RepSox-SMCs compared to the other treatments (FIG. 2C). We compared the present methods with a previous protocol that generated 80% MYH11+ SMCs (Cheung et al., 2012) (FIG. 9A). RT-qPCR data revealed that RepSox induced a 23 fold improvement of MYH11 expression (FIG. 9B). Immunocytochemistry revealed that RepSox-SMCs also expressed other structural proteins, SMA and SM22α (FIG. 2E), and RT-qPCR analysis revealed that RepSox-SMCs expressed higher level of structural genes, including SMTN, CNN1, MYH11 and ELN compared to PDGF-BB and TGF-β1 treated cells (FIG. 2F). The expression of ACTA2 (SMA) and TAGLN (SM22α) was similar between RepSox-SMCs and T-SMCs, and both were higher than other cells. In contrast, the expression of collagen (COL1A1), a major ECM gene increased in the synthetic state (Wanj are et al., 2013; Yang et al., 2016), was lower in RepSox-SMCs compared to P-SMCs, T-SMCs, and PT-SMCs. Taken together, RepSox-SMCs expressed higher levels of contractile genes and produced less ECM.

Figures 10A, 10B, 10C:
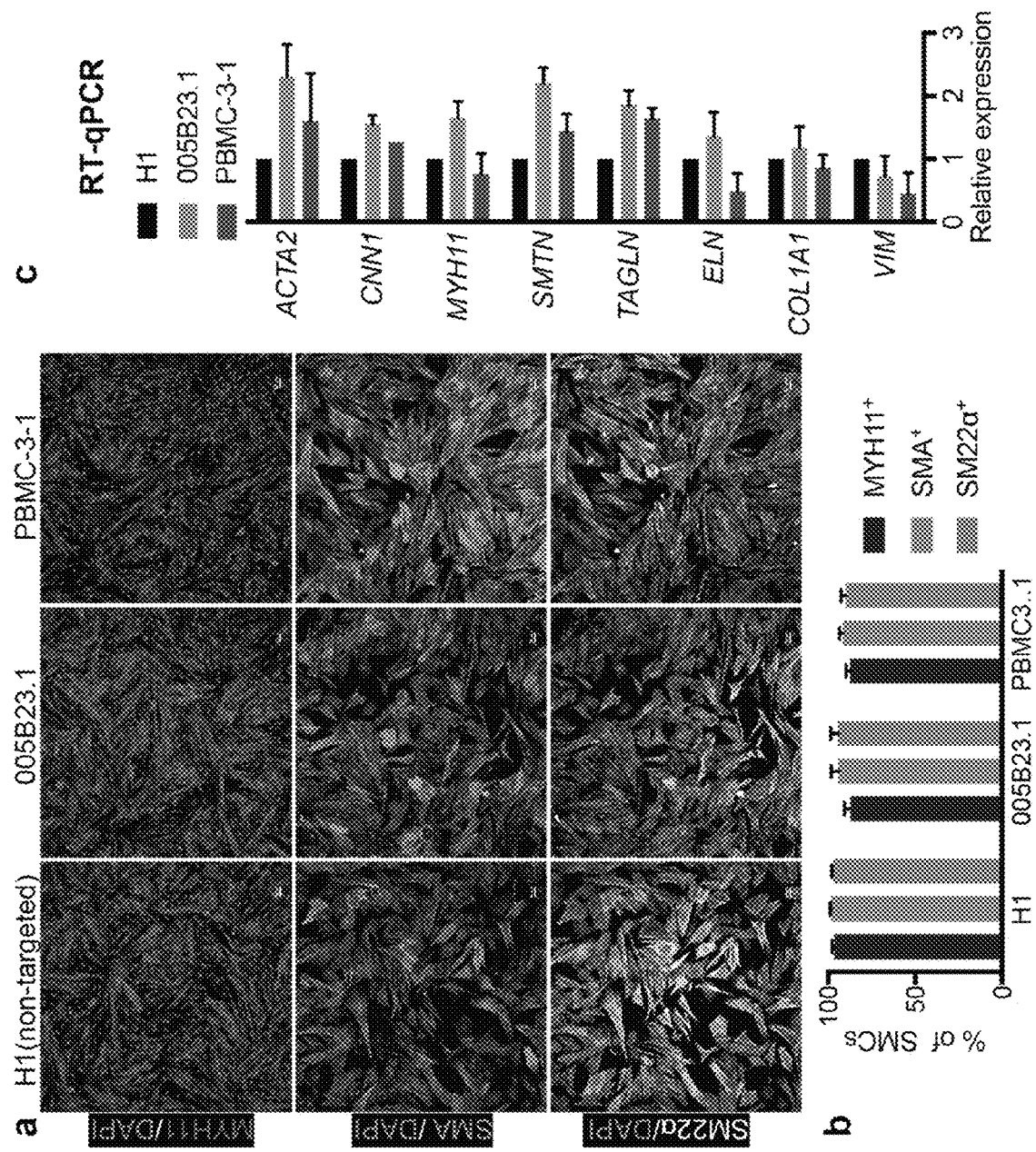
FIGS. 10A-10C show generation of SMCs from multiple pluripotent stem cell lines.

The RepSox-SMC differentiation protocol described herein also worked robustly for induced-pluripotent stem (iPS) cell lines, 005B23.1 and PBMC-3-1, which were derived from skin punch fibroblasts and peripheral blood mononuclear cells respectively. The results revealed that 87%-98% of MYH11$^+$, SMA$^+$, or SM22α$^+$ SMCs were generated from these two iPS cell lines and non-targeted H1 ES cells (FIGS. 10A and 10B). In addition, RT-qPCR revealed that the overall expression of the contractile genes and ECM genes were similar between iPS cell- and ES cell-derived SMCs (FIG. 10C).

Figures 3A, 3B, 3C, 3D, 3E, 3F, 3G, 3H, 3I, 3J, 3K:
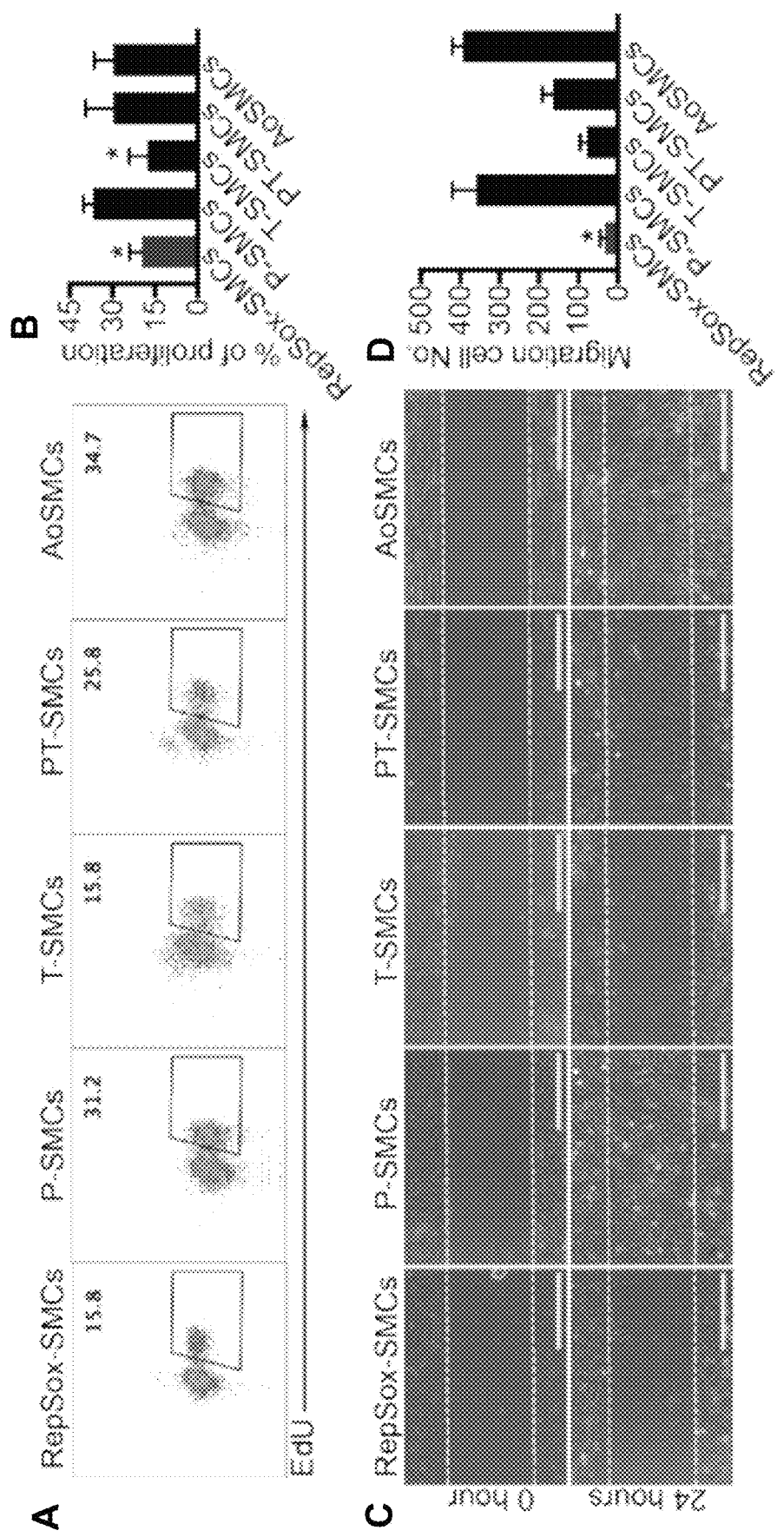
FIGS. 3A-3K show functional characterization of SMCs.
Figures 3A, 3B, 3C, 3D, 3E, 3F, 3G, 3H, 3I, 3J, 3K:
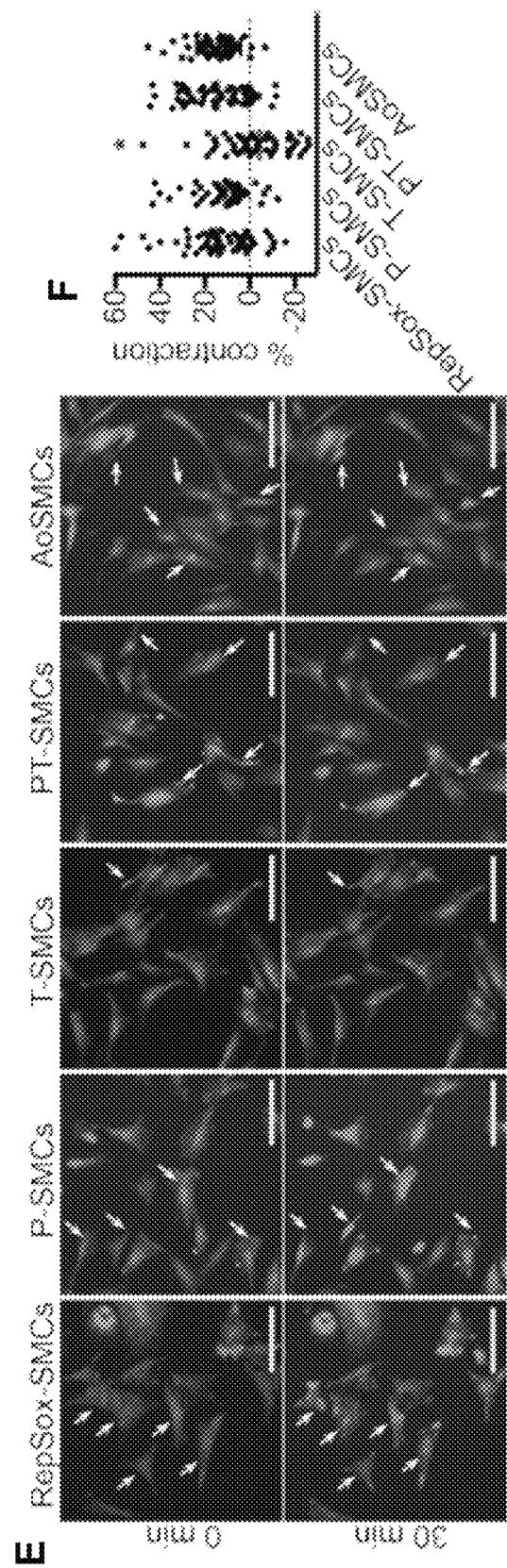
Figures 3A, 3B, 3C, 3D, 3E, 3F, 3G, 3H, 3I, 3J, 3K:
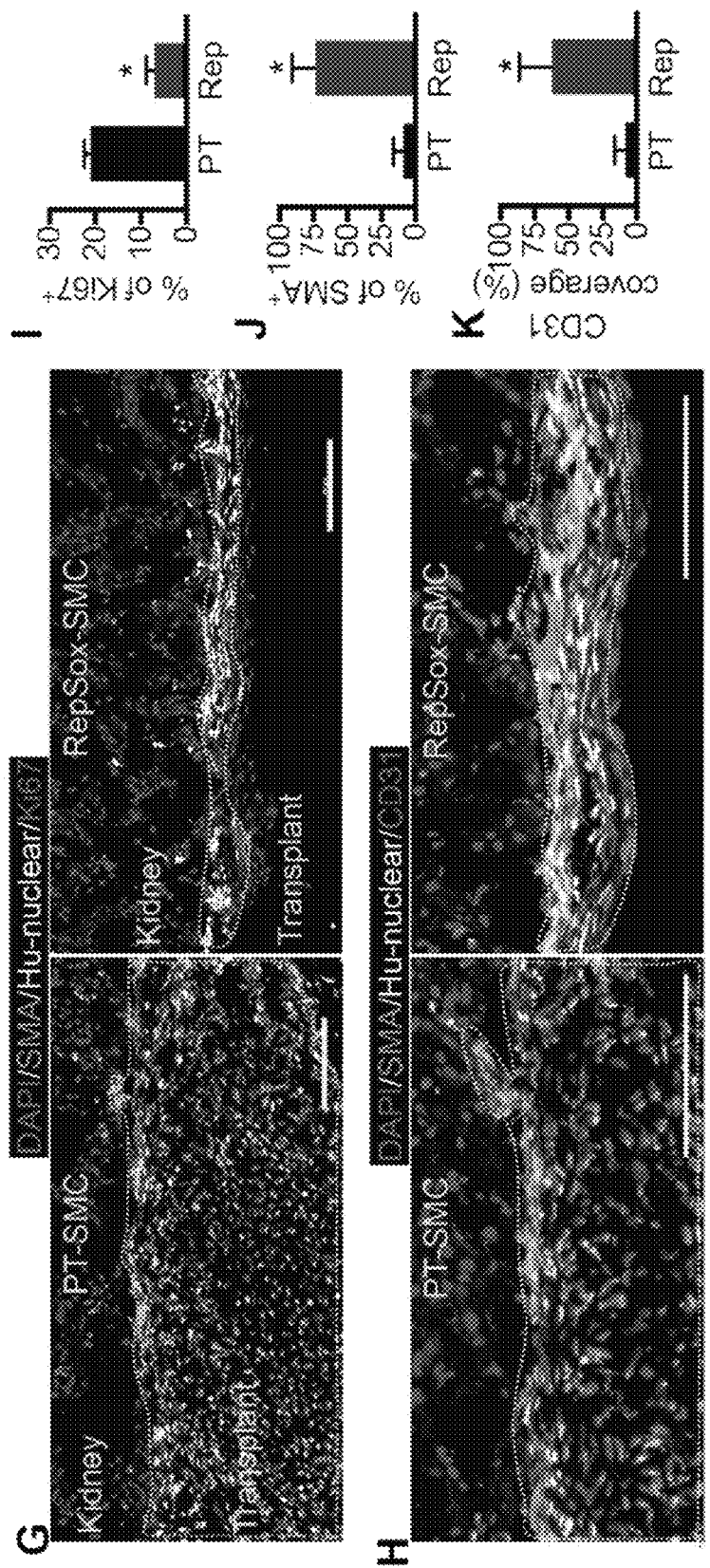

RepSox-SMCs have a contractile phenotype—Since low proliferation and migration rates are characteristic of contractile SMCs, we characterized these properties in pluripotent stem cell-derived SMCs and AoSMCs. RepSox-SMCs and T-SMCs had lower proliferation rates than the other SMC groups (FIG. 3A), and RepSox-SMCs showed the lowest migration rate compared to all the other SMC groups (FIG. 3B). SMC contraction controls vascular tone and blood pressure (Brozovich et al., 2016), thus we also measured carbachol-evoked cell contraction. Time-lapse imaging revealed that P-SMC, PT-SMC, RepSox-SMCs, and AoSMC exhibited a 10-20% change of cell surface area after carbachol treatment (FIG. 3C). However, the average T-SMC actually expanded during the treatment (FIG. 3C), suggesting that T-SMCs don't have physiological normal contractile properties. In summary, RepSox treatment produced a more contractile SMC phenotype, including lower proliferation and migration rates.

To test whether RepSox-SMCs maintained the contractile phenotype in vivo, RepSox-SMCs and PT-SMCs were transplanted into mouse kidneys within the capsule. Immunostaining showed RepSox-SMCs have a lower proliferation rate compared to PT-SMCs (FIGS. 3G and 3I). Additionally, most PT-SMCs lost SMA expression (FIGS. 3G, 3H, and 3J, highlighted) and didn't recruit endothelial cells (FIGS. 3H and 3K, highlighted). In contrast, most RepSox-SMCs (75%) maintained SMA expression (FIGS. 3G, 3H, and 3J) and they were able to recruit more endothelial cells than PT-SMCs, as demonstrated by endothelial cell coverage (FIGS. 3H and 3K). Thus, RepSox-SMCs are more contractile than PT-SMCs in vivo.

Figure 11A:
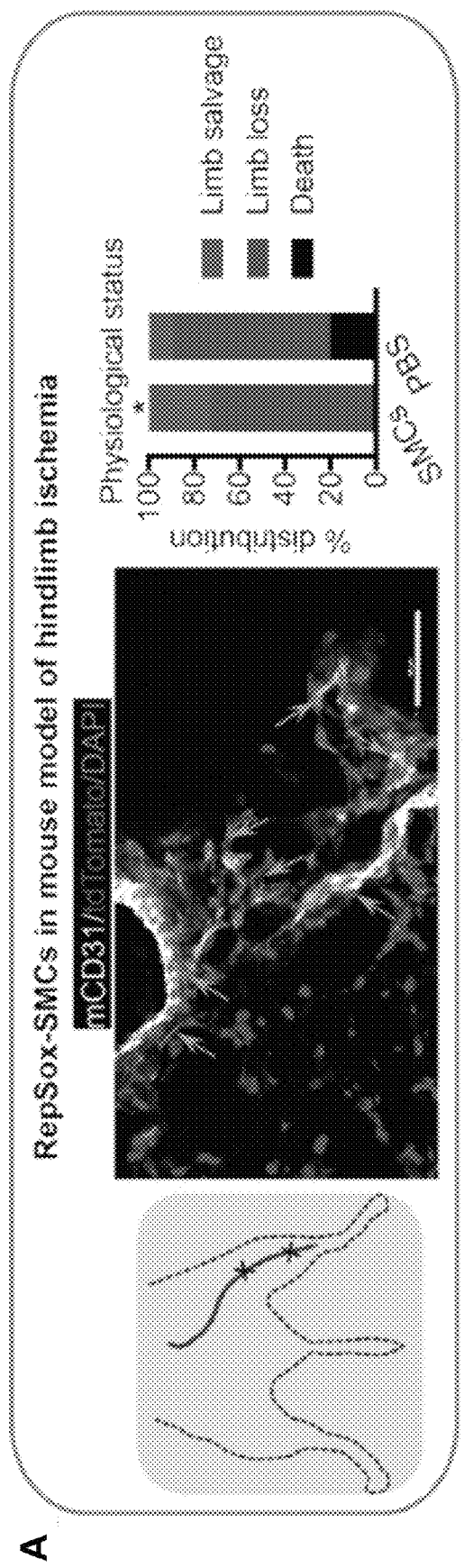
FIGS. 11A-11B show the use of RepSox-SMCs in a mouse hind limb ischemic model.
Figure 11B:
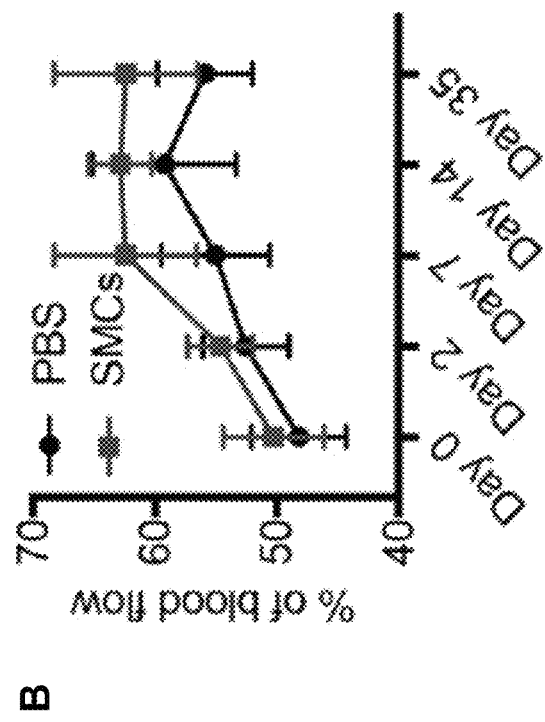

Targeting endogenous SMCs is a suggested therapeutic strategy for stimulating angiogenesis (Yin et al., 2015), but the therapeutic effect of transplanting SMCs alone is unclear. Hence, we transplanted RepSox-SMCs into a mouse limb ischemia model. The average blood flow was higher in RepSox-SMCs treated mice, but the difference was not statistically significant (FIG. 11B). However, RepSox-SMCs did become associated with mouse endothelial cells (FIG. 11A), and Rep Sox-SMCs treatment increased limb salvage and animal survival (FIG. 11A), demonstrating that the transplantation of RepSox-SMCs could have therapeutic value.

Figures 4A, 4B, 4C, 4D, 4E, 4F, 4G:
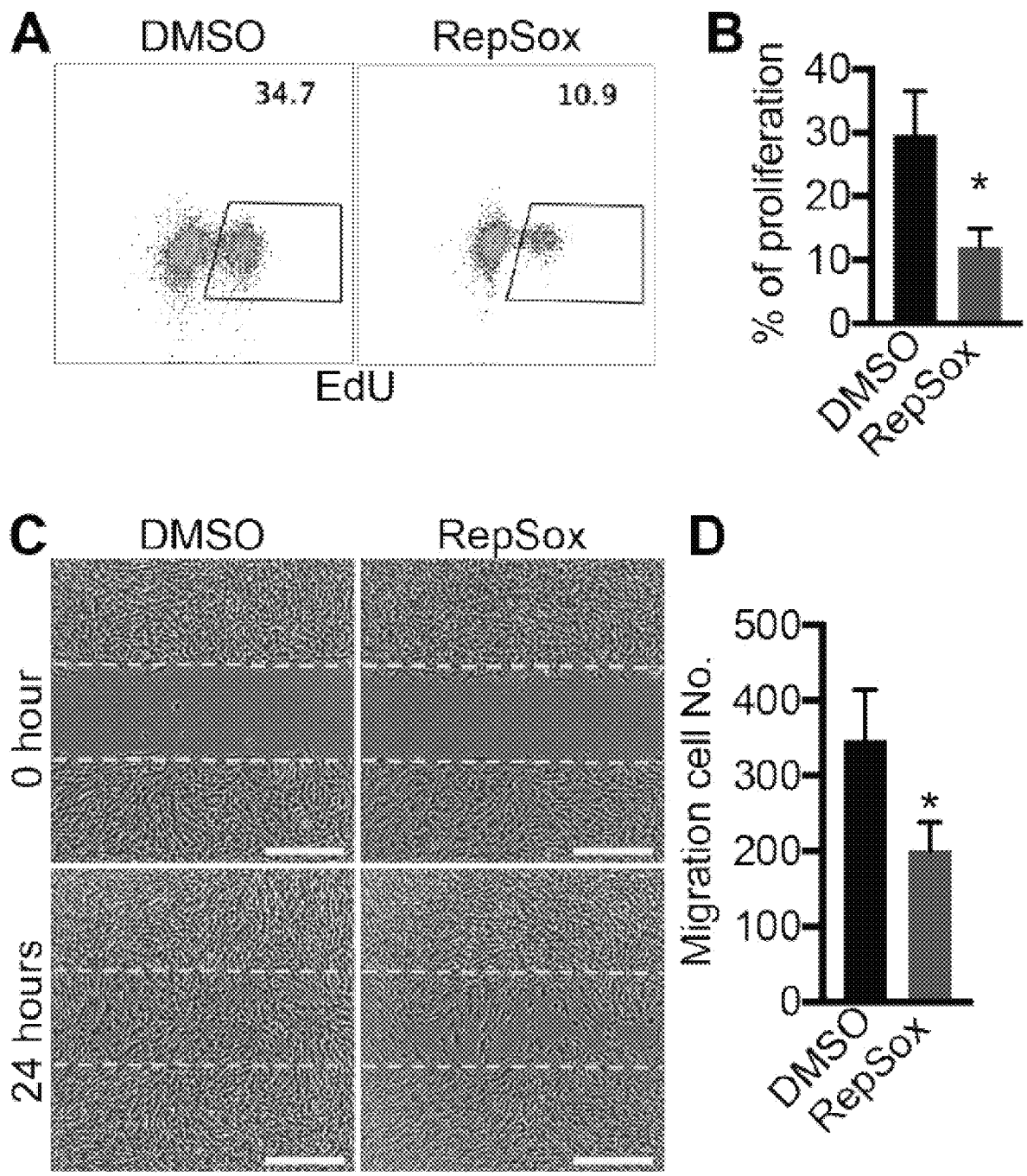
FIGS. 4A-4G show that RepSox restores contractile SMC phenotype.
Figures 4A, 4B, 4C, 4D, 4E, 4F, 4G:
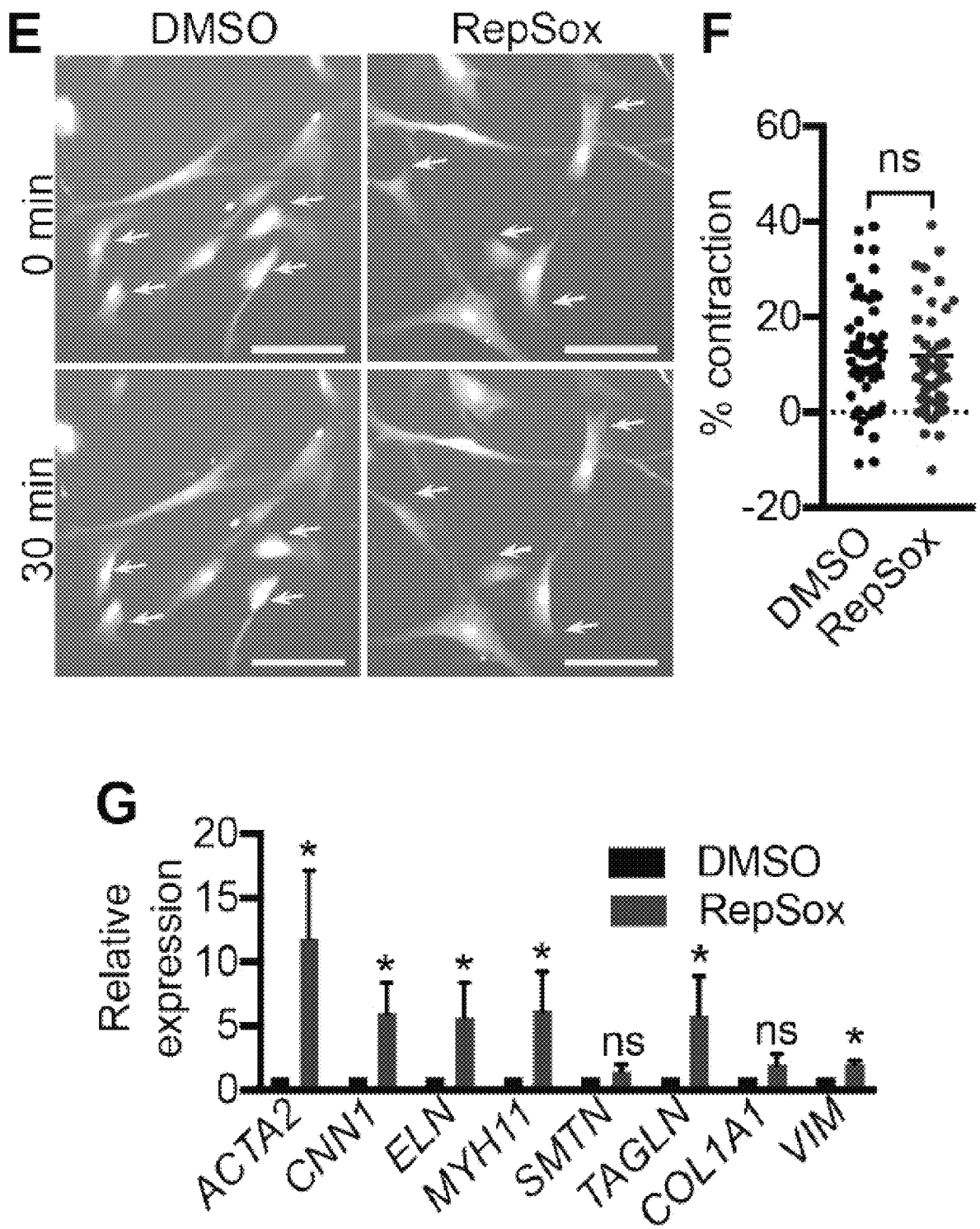

High-throughput screening identifies small molecules that inhibit intimal hyperplasia—We next investigated whether our screening identified small molecules that can promote the contractile phenotype of SMCs in vivo and inhibit intimal hyperplasia. Indeed, among the hits (FIG. 1C), UO126, Y27632, and retinoic acid have been shown to inhibit intimal hyperplasia in previous studies (DeRose et al., 1999; Gulkarov et al., 2009; Sawada et al., 2000). Since RepSox induced the best contractile SMC differentiation, we first tested whether RepSox could promote synthetic to contractile phenotype switching in vitro. Cultured primary AoSMCs undergo a contractile to synthetic switch upon culture (Beamish et al., 2010; Owens et al., 2004), so we tested whether RepSox would reverse this switch. RepSox treatment reduced cell migration and proliferation rates of AoSMCs without affecting contraction ability (FIGS. 4A-4F). However, RepSox treatment did increase contractile gene expression (FIG. 4G). These results suggest that RepSox can promote the contractile phenotype of primary AoSMCs.

Figures 5A, 5B, 5C, 5D, 5E, 5F, 5G, 5H, 5I, 5J:
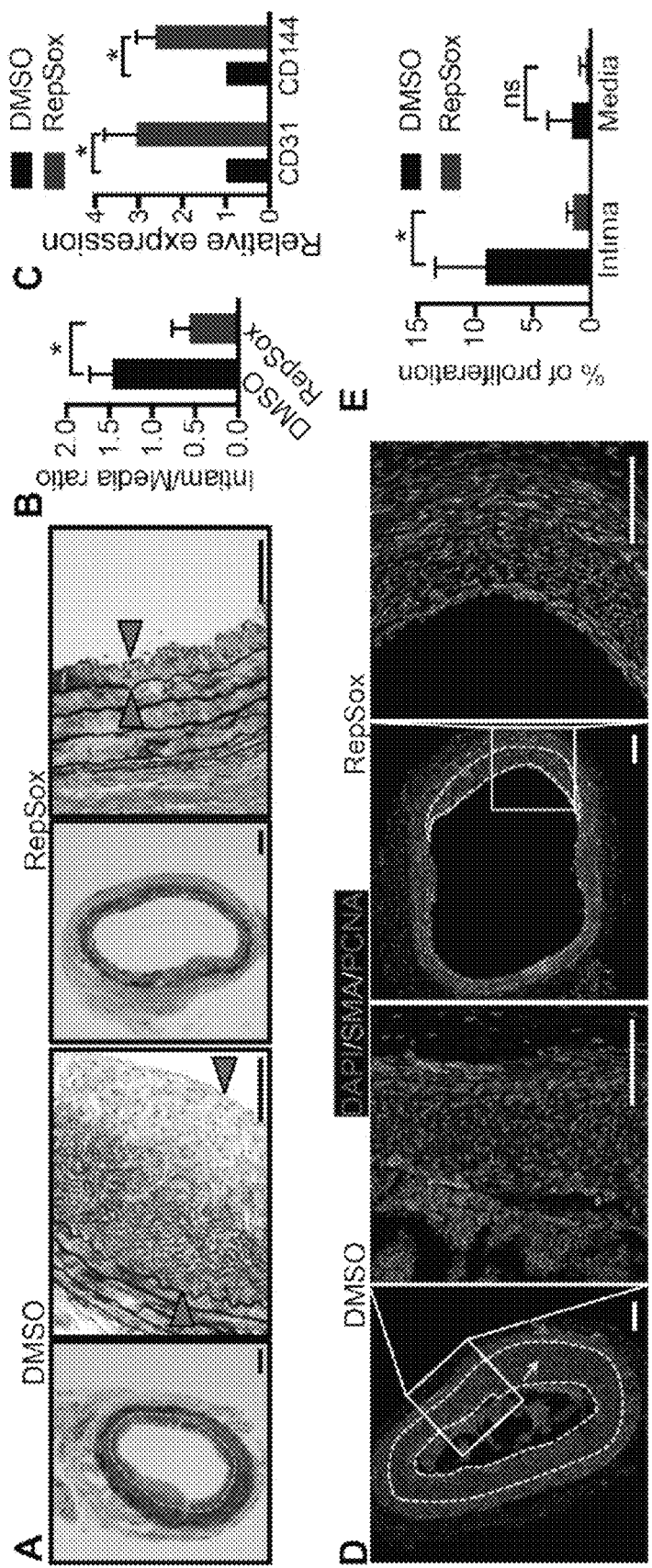
FIGS. 5A-5J depict RepSox inhibition of intimal hyperplasia in a rat balloon injury model.
Figures 5A, 5B, 5C, 5D, 5E, 5F, 5G, 5H, 5I, 5J:
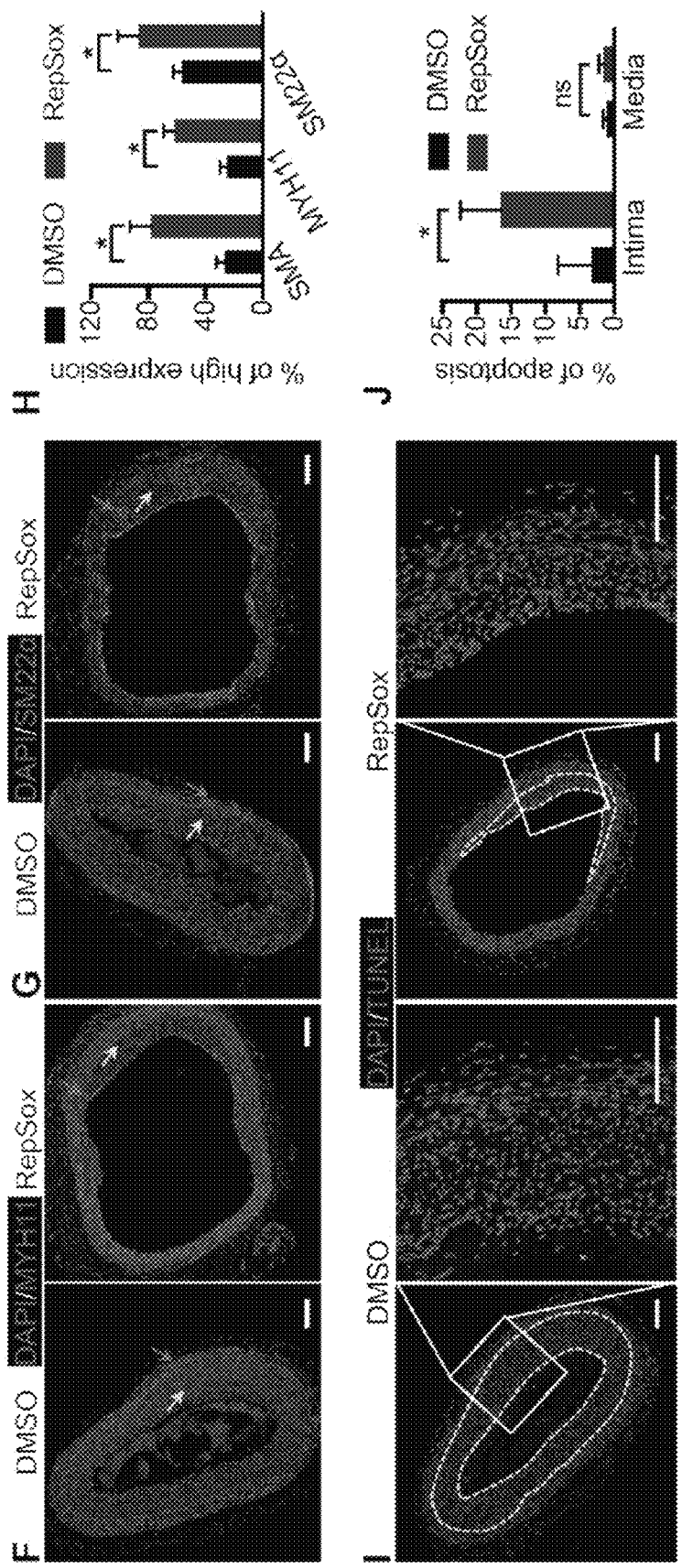
Figures 6A, 6B, 6C, 6D, 6E, 6F, 6G, 6H:
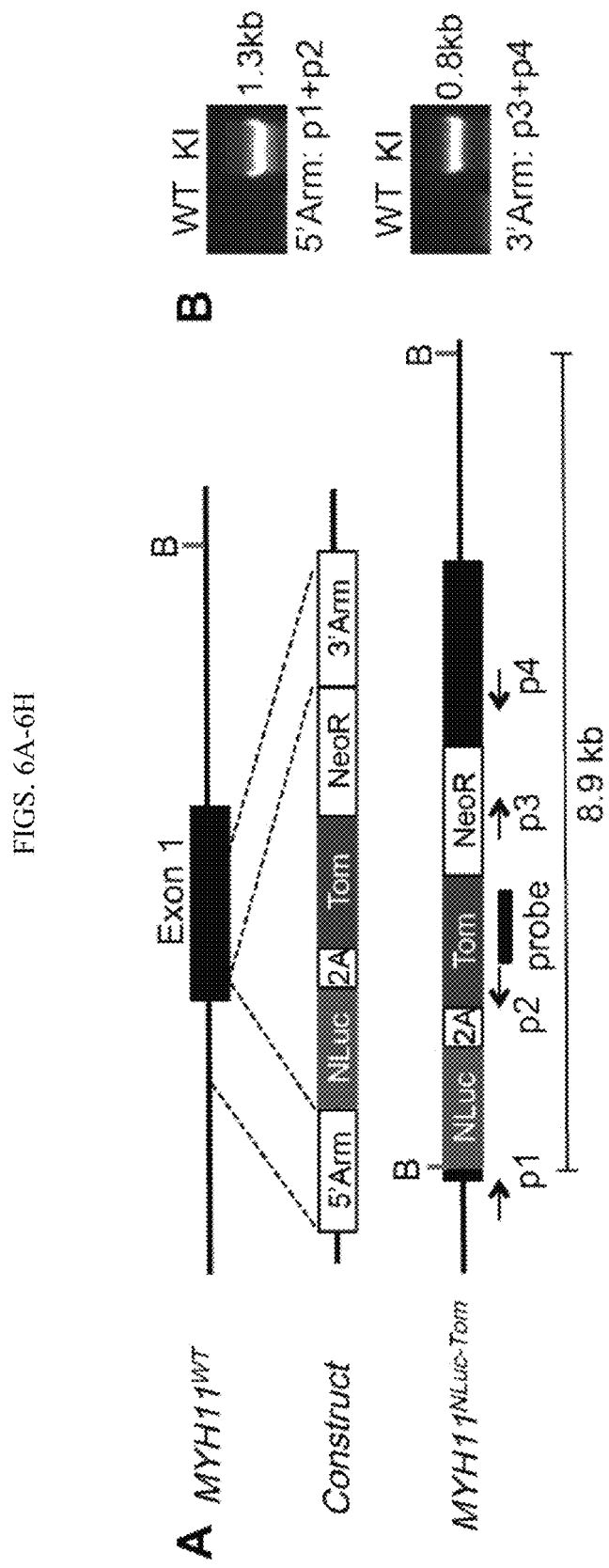
FIGS. 6A-6H show generation and characterization of the reporter cell line.
Figures 6A, 6B, 6C, 6D, 6E, 6F, 6G, 6H:
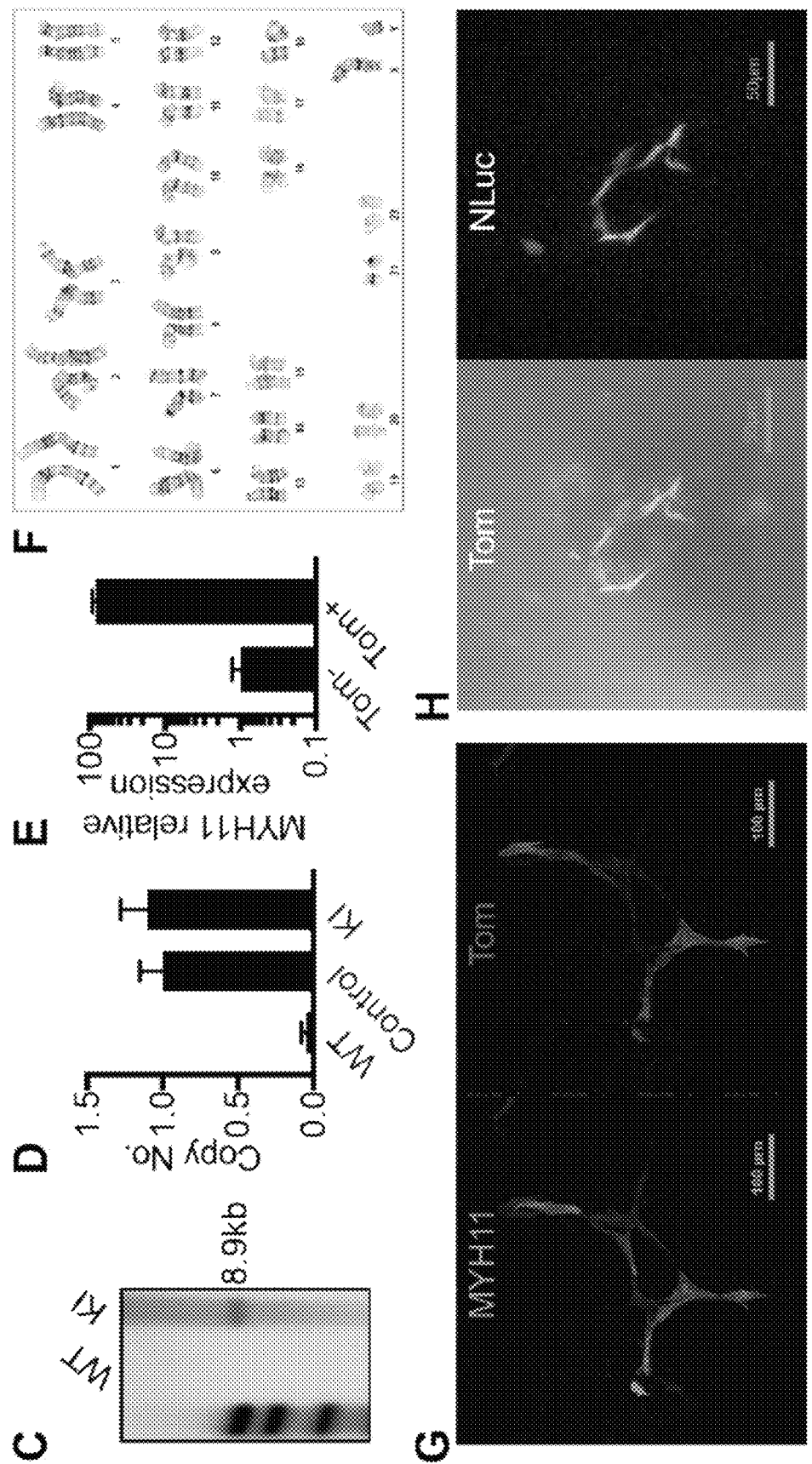

We next examined the function of RepSox in a rat intimal hyperplasia model. In order to reduce any side effect induced by systematic drug delivery, RepSox or DMSO was dissolved in gel and then applied to the outside of the injured artery segment immediately after balloon injury of the rat carotid artery (Shi et al., 2014). Carotid arteries were collected and sectioned 14 days after surgery. H&E staining revealed a pronounced neointima formation in the control group (DMSO), that was reduced by treatment with RepSox from 1.5 to 0.5 (intima/media ratio, FIGS. 5A and 5B). The clinically-used anti-restenotic drugs rapamycin (or analogs) and paclitaxel suppressed endothelium repair (Prasad et al., 2005; Zheng et al., 2014). To test the effect of RepSox, we performed qPCR analysis. The result revealed that RepSox increased endothelia cell marker expression (FIG. 5C), suggesting that RepSox might promote endothelium repair. To further understand how RepSox reduced intimal hyperplasia, immunostaining was performed. The results revealed that RepSox decreased proliferation in intima but not media layer (FIGS. 5D and 5E). In addition, the expression of contractile proteins, SMA, MYH11, and SM22α, was significantly increased (FIGS. 5D, 5F, 5G, and 5H). In contrast, the apoptosis was increased in intima by RepSox treatment (FIGS. 5I and 5J). Thus, RepSox inhibited intimal hyperplasia in vivo and might have therapeutic value for reducing restenosis in vascular procedures.

Discussion

To reduce intimal hyperplasia, drug eluting stents release drugs that target either inflammation or cell proliferation (Pendyala et al., 2008). The clinically used anti-restenotic drugs, rapamycin (or analogs) and paclitaxel, are proliferation antagonists without cell type specificity (Prasad et al., 2005; Zheng et al., 2014). Here, in an attempt to identify agents that would be more cell type specific, we screened for drugs that could reduce intimal hyperplasia by forcing more terminal differentiation of less differentiated synthetic SMCs to a contractile state. Interestingly, three compounds identified in our screening UO126, Y27632, and retinoic acid have been demonstrated to inhibit intimal hyperplasia in previous studies (DeRose et al., 1999; Gulkarov et al., 2009; Sawada et al., 2000).

To our knowledge, RepSox has not previously been identified as an inhibitor of intimal hyperplasia, and it is the most potent inducer of the contractile state that we identified in our assay. RepSox's ability to reduce intimal hyperplasia in the rat balloon injury model also suggests a therapeutic value. However, to date we have been unable to identify the direct molecular target of RepSox in our system. RepSox was previously reported to be a TGFβ signaling inhibitor (Ichida et al., 2009), but our results suggest that TGFβ signaling may not be the target that modulates SMC differentiation. Identifying the target should facilitate a better understanding of the mechanisms underlying vascular disease, and enhance the therapeutic value of this compound or related compounds sharing the same target.

The protocol described here for differentiating contractile SMCs from human ES cells is efficient and utilizes xeno-free medium. In particular, replacing PDGF-BB and TGF-β1 with RepSox resulted in SMCs that exhibited a more contractile, less proliferative phenotype, suggesting that these cells might be used to produce tissue engineered blood vessels less prone to intimal hyperplasia and stenosis. In addition, transplantation of RepSox-SMCs in limb ischemia model improved animal survival and limb salvage, suggesting that these SMC's might have therapeutic value by themselves. With the advent of human iPS cells (Takahashi et al., 2007; Yu et al., 2007), it is now possible to generate these cells either from a specific patient or from individuals with defined genetic backgrounds selected to minimize immune rejection in groups of patients. However, the timeline and cost for a patient-specific therapy is likely to be excessive. One strategy that has been suggested is to create banks of HLA-homozygous iPS cell lines that would reduce immune rejection when transplanted to HLA-heterozygous (haplomatched) individuals (de Rham and Villard, 2014; Riolobos et al., 2013). It will be particularly important to establish how much value the HLA-homozygous banking strategy has in modulating the immune rejection of SMCs, as these cells may ultimately be transplanted by themselves, within tissue engineered blood vessels, or as part of a vascular supply of a larger tissue-engineered construct.

The present invention has been described in terms of one or more preferred embodiments, and it should be appreciated that many equivalents, alternatives, variations, and modifications, aside from those expressly stated, are possible and within the scope of the invention.

We claim:

1. A tissue-engineered blood vessel comprising an isolated population of contractile smooth muscle cells that does not undergo contractile-to-synthetic phenotype switching, wherein the isolated population of contractile smooth muscle cells is obtained by a method comprising:
   (1) obtaining smooth muscle cell (SMC) progenitor cells; and
   (2) culturing the SMC progenitor cells in a culture medium comprising a myosin heavy chain 11 (MYH11) agonist, wherein the MYH11 agonist is RepSox, until a cell population comprising MYH11+, alpha-actin 2 positive (ACTA2+), smoothelin positive (SMTN+), calponin1 positive (CNN1+), and transgelin positive (TAGLN+) contractile smooth muscle cells is obtained, and wherein the SMC progenitor cells are obtained by a method selected from the group consisting of:
   (a) a first method comprising:
      (i) culturing mesoderm cells under conditions and for a time sufficient to obtain a population of cells expressing MEOX1;
      (ii) culturing the population of cells expressing MEOX1 under conditions and for a time sufficient to suppress MEOX1 expression; and
      (iii) culturing the population of cells from step (ii) under conditions and for a time sufficient to obtain a population of SMC progenitor cells, and
   (b) a second method comprising:
      (i) culturing mesoderm cells in chemically defined medium that comprises a fibroblast growth factor (FGF) or a vascular endothelial growth factor (VEGF) for a period of time sufficient to induce SMC progenitor cells; and
      (ii) culturing the population of cells from step (i) under conditions and for a time sufficient to obtain a population of SMC progenitor cells.

2. The tissue-engineered blood vessel of claim 1, wherein the SMC progenitors are obtained by the first method and wherein in step (i) the mesoderm cells are cultured in chemically defined medium comprising transforming growth factor β1 (TGF β1) in an amount sufficient to obtain a population of cells expressing MEOX1.

3. The tissue-engineered blood vessel of claim 1, wherein the SMC progenitors are obtained by the first method and wherein in step (ii) the MEOX1-expressing cells are cultured in chemically defined medium comprising a FGF or a VEGF in an amount sufficient to suppress MEOX1 expression.

4. The tissue-engineered blood vessel of claim 1, wherein the SMC progenitors are obtained by the first method and wherein in step (iii) the population of cells from step (ii) is cultured in chemically defined medium comprising FGF2 or VEGF A for a period of time sufficient to induce SMC progenitor cells.

5. The tissue-engineered blood vessel of claim 1, wherein the SMC progenitors are obtained by the second method and wherein in step (i) the mesodermal cells are cultured in chemically defined medium comprising FGF2 or VEGF A for about 5 days.

6. The tissue-engineered blood vessel of claim 1, wherein the SMC progenitors are obtained by the second method and wherein in step (i) the mesoderm cells are cultured in chemically defined medium comprising FGF2 or VEGF A for a period of time sufficient to produce SMC progenitor cells.

7. The tissue-engineered construct of claim 6, wherein the chemically defined medium additionally comprises a NOTCH pathway agonist.

8. The tissue-engineered blood vessel of claim 1, wherein the SMC progenitors are obtained by the first method comprising:
   (i) culturing mesoderm cells under conditions and for a time sufficient to obtain a population of cells expressing MEOX1;
   (ii) culturing the population of cells expressing MEOX1 under conditions and for a time sufficient to suppress MEOX1 expression; and
   (iii) culturing the population of cells from step (ii) under conditions and for a time sufficient to obtain a population of SMC progenitor cells.

9. The tissue-engineered blood vessel of claim 1, wherein the SMC progenitors are obtained by the second method comprising:
- (i) culturing mesoderm cells in chemically defined medium that comprises a fibroblast growth factor (FGF) or a vascular endothelial growth factor (VEGF) for a period of time sufficient to induce SMC progenitor cells; and
- (ii) culturing the population of cells from step (i) under conditions and for a time sufficient to obtain a population of SMC progenitor cells.

10. A tissue-engineered construct comprising an isolated population of contractile smooth muscle cells that does not undergo contractile-to-synthetic phenotype switching, wherein the isolated population of contractile smooth muscle cells is obtained by a method comprising:
- (1) obtaining smooth muscle cell (SMC) progenitor cells; and
- (2) culturing the SMC progenitor cells in a culture medium comprising a myosin heavy chain 11 (MYH11) agonist, wherein the MYH11 agonist is Rep-Sox, until a cell population comprising MYH11+, alpha-actin 2 positive (ACTA2+), smoothelin positive (SMTN+), calponin1 positive (CNN1+), and transgelin positive (TAGLN+) contractile smooth muscle cells is obtained, and wherein the SMC progenitor cells are obtained by a method selected from the group consisting of:
- (a) a first method comprising:
  - (i) culturing mesoderm cells under conditions and for a time sufficient to obtain a population of cells expressing MEOX1;
  - (ii) culturing the population of cells expressing MEOX1 under conditions and for a time sufficient to suppress MEOX1 expression; and
  - (iii) culturing the population of cells from step (ii) under conditions and for a time sufficient to obtain a population of SMC progenitor cells, and
- (b) a second method comprising:
  - (i) culturing mesoderm cells in chemically defined medium that comprises a fibroblast growth factor (FGF) or a vascular endothelial growth factor (VEGF) for a period of time sufficient to induce SMC progenitor cells; and
  - (ii) culturing the population of cells from step (i) under conditions and for a time sufficient to obtain a population of SMC progenitor cells.

11. The tissue-engineered construct of claim 10, wherein the SMC progenitors are obtained by the first method and wherein in step (i) the mesoderm cells are cultured in chemically defined medium comprising transforming growth factor β1 (TGF β1) in an amount sufficient to obtain a population of cells expressing MEOX1.

12. The tissue-engineered construct of claim 10, wherein the SMC progenitors are obtained by the first method and wherein in step (ii) the MEOX1-expressing cells are cultured in chemically defined medium comprising a FGF or a VEGF in an amount sufficient to suppress MEOX1 expression.

13. The tissue-engineered construct of claim 10, wherein the SMC progenitors are obtained by the first method and wherein in step (iii) the population of cells from step (ii) is cultured in chemically defined medium comprising FGF2 or VEGF A for a period of time sufficient to induce SMC progenitor cells.

14. The tissue-engineered construct of claim 10, wherein the SMC progenitors are obtained by the second method and wherein in step (i) the mesodermal cells are cultured in chemically defined medium comprising FGF2 or VEGF A for a period of time sufficient to produce SMC progenitor cells.

15. The tissue-engineered construct of claim 14, wherein the chemically defined medium additionally comprises a NOTCH pathway agonist.

16. The tissue-engineered construct of claim 10, wherein the SMC progenitors are obtained by the first method comprising:
- (i) culturing mesoderm cells under conditions and for a time sufficient to obtain a population of cells expressing MEOX1;
- (ii) culturing the population of cells expressing MEOX1 under conditions and for a time sufficient to suppress MEOX1 expression; and
- (iii) culturing the population of cells from step (ii) under conditions and for a time sufficient to obtain a population of SMC progenitor cells.

17. The tissue-engineered construct of claim 10, wherein the SMC progenitors are obtained by the second method comprising:
- (iii) culturing mesoderm cells in chemically defined medium that comprises a fibroblast growth factor (FGF) or a vascular endothelial growth factor (VEGF) for a period of time sufficient to induce SMC progenitor cells; and
- (iv) culturing the population of cells from step (i) under conditions and for a time sufficient to obtain a population of SMC progenitor cells.

* * * * *